United States Patent [19]
Shennib

[11] Patent Number: 5,923,764
[45] Date of Patent: Jul. 13, 1999

[54] VIRTUAL ELECTROACOUSTIC AUDIOMETRY FOR UNAIDED SIMULATED AIDED, AND AIDED HEARING EVALUATION

[75] Inventor: Adnan Shennib, Fremont, Calif.

[73] Assignee: Decibel Instruments, Inc., Fremont, Calif.

[21] Appl. No.: 08/769,186

[22] Filed: Dec. 18, 1996

Related U.S. Application Data

[63] Continuation of application No. 08/292,073, Aug. 17, 1994, abandoned.

[51] Int. Cl.$^6$ .................................................. H04R 39/00
[52] U.S. Cl. ............................................. 381/60; 381/23.1
[58] Field of Search ...................................... 381/23.1, 60

[56] References Cited

U.S. PATENT DOCUMENTS

| | | | |
|---|---|---|---|
| 4,118,599 | 10/1978 | Iwahara et al. | 179/1 |
| 4,139,728 | 2/1979 | Haramoto et al. | 179/1 |
| 4,219,696 | 8/1980 | Kogure et al. | 179/1 |
| 4,759,070 | 7/1988 | Voroba et al. | 381/60 |
| 4,774,515 | 9/1988 | Gehring | 242/53 |
| 4,809,708 | 3/1989 | Geisler et al. | 128/746 |
| 5,173,944 | 12/1992 | Begault | 381/17 |

OTHER PUBLICATIONS

Mueller, H. Gustav; "A Practical Guide to Today's Bonanza of Underused High–Tech Hearing Products," The Hearing Journal, Mar. 1993, vol. 46, No. 3, pp. 13–27.

Hawkins, David B., Ph.D.; Probe Microphone Measurements: Hearing Aid Selection and Assessment, Chapter 5, "Prescriptive Approaches to Selection of Gain and Frequency Response", pp. 91–112.

Mowrer, Donald E., Ph.D. and Steams, Carol; "Threshold measurement variability among hearing aid dispensers," Hearing Instruments, vol. 43, No. 4, 1992, pp. 26–27.

Gauthier, E.A. and Rapisardi, D.A., MS; "A threshold is a threshold is a threshold . . . or is it?", Hearing Instruments, vol. 43, No. 3, 1992, pp. 26–27.

(List continued on next page.)

*Primary Examiner*—Thomas D. Lee
*Assistant Examiner*—Stephen Brinich
*Attorney, Agent, or Firm*—Michael A. Glenn

[57] ABSTRACT

A hearing evaluation and hearing aid fitting system provides a fully immersive three-dimensional acoustic environment to evaluate unaided, simulated aided, and aided hearing function of an individual. Digital filtering of signal sources representing speech and other sound stimuli according to selected models and signal processing parameters, such as audio sources, spatializing coordinates, acoustic boundaries, hearing aid simulations, and individualized transfer functions synthesizes a simulated acoustic condition for presentation to an individual for objective and subjective hearing evaluation. An intra-canal prosthesis incorporating a microphone probe is positioned in the ear canal to measure in-the-ear-canal responses at a common reference point near the tympanum during unaided, simulated aided, and aided hearing evaluation to provide measurements that directly correlate across all phases of hearing assessment during hearing aid fitting. A virtual electroacoustic audiometer computes hearing aid prescription based on unaided evaluation results and various reference measurements including in-the-ear canal responses to acoustic stimuli. The system synthesizes signals reflecting the combination of an audio signal model, spatialization model, and acoustic boundary model, as well as hearing aid model in the case of simulated aided condition. Once an optimal simulated hearing aid model is selected, based on a number of criteria including optimal performance, sound, restoration, listening preference, type, size, controls, and life-style factors, a detailed hearing aid specification is derived and provided to the dispenser/manufacturer for assembly. A modular hearing aid according to the results of such hearing assessment is also provided that includes highly configurable electroacoustic and electronic signal processing elements.

32 Claims, 28 Drawing Sheets

OTHER PUBLICATIONS

Earphone Calibration, "Real Ear Methods", p. 26.

Valente, M; Potts, L; and Vass, Bill; "Intersubject Variability of the Real–Ear SPL: TDH–39P vs ER 3A Earphones".

Cherry, E. Colin; "Som Experiments on the Recognition of Speech, with One and with Two Ears," The Journal of the Acoustical Society of America, vol. 25, No. 5, Sep. 1953, pp. 975–979.

Cherry, E. Colin and Taylor, W.K; "Some Further Experiments upon the Recognition of Speech, with One and with Two Ears," The Journal of the Acoustical Society of America, vol. 26, No. 4, Jul. 1994, pp. 554–559.

Bronkhorst, A.W. and Plomp, R.; "The effect of head–induced interaural time and level differences on speech intelligibility in noise," J. Acoust. Soc. Am. 83 (4), Apr. 1988, pp. 1508–1516.

Bronkhorst, A.W. and Plomp, R.; "Effect of multiple speech-like maskers on binaural speech recognition in normal and impaired hearing,". Acoust. Soc. Am. 92 (6), Dec. 1992, pp. 3132–3139.

Begault, Durand R.; "Call Signal Intelligibility Improvement Using a Spatial Auditory Display," NASA Technical Memorandum 104014, Apr. 1993.

Chen, Jospeh K. and Geisler, C. Daniel, "Estimation of eardrum acoustic pressure and of ear canal length from remote points in the canal,". Acoust. Soc. Am. 87 (3), Mar. 1990, pp. 1237–1247.

Sandberg, Robert, MS; McSpaden, Jay B., Ph.D.; and Allen, Dan, MA; "Real measurement from real ear equipment," Hearing Instruments, vol. 42, No. 3, 1993, pp. 17–18.

"Selection instrumentation/master hearing aids in review," Hearing Instruments, vol. 39, No. 3, 1988, pp. 18–20.

"ITS—Hearing Aid Simulator," software brochure.

Wightman, Frederic L. and Kistler, Doris J.; "Headphone simulation of free–field listening. I: Stimulus synthesis,". Acoust. Soc. Am. 85 (2), Feb. 1989, pp. 858–867.

Wightman, Frederic L. and Kistler, Doris J.; "Headphone simulation of free–field listening. II: Psychophysical validation.". Acoust. Soc. Am. 85 (2). Feb. 1989. pp. 868–878.

Begault, Durand R. and Wenzel, Elizabeth M., NASA Ames Research Center, Moffett Field, California, "Headphone Localization of Speech," Human Factors, 1993, 35(2), 361–376.

American National Standard, Specification of Hearing Aid Characteristics, ANSI S3.22–1987.

"three–dimensional audio for PC–compatibles," The Beachtron, "Beachtron User's Guide", Crystal River Engineering, Inc.

Zdeblick, Mark J., Ph.D., "A Revolutionary Actuator for Microstructures," reprint from Sensors, Feb. 1993.

Mills, A.W., "On the Minimum Audible Angle,". Acoust. Soc. Am., vol. 30, No. 4, Apr. 1953, pp. 237–246.

Rife, Douglas D. and Vanderkooy, John; "Transfer–Function Measurement with Maximum–Length Sequences," J. Audio Eng. Soc., vol. 37, No. 6, Jun. 1989, pp. 419–442.

American National Standard, Specification for Audiometers, ANSI S3.6.1989.

Jamieson, Donald G., "Consumer–Based Electroacoustic Hearing Aid Measures," JSLPA Monogr. Suppl. 1, Jan. 1993, pp. 87–98.

Assessment of Fitting, Arrangements, Special Circuitry, and Features, pp. 221–224.

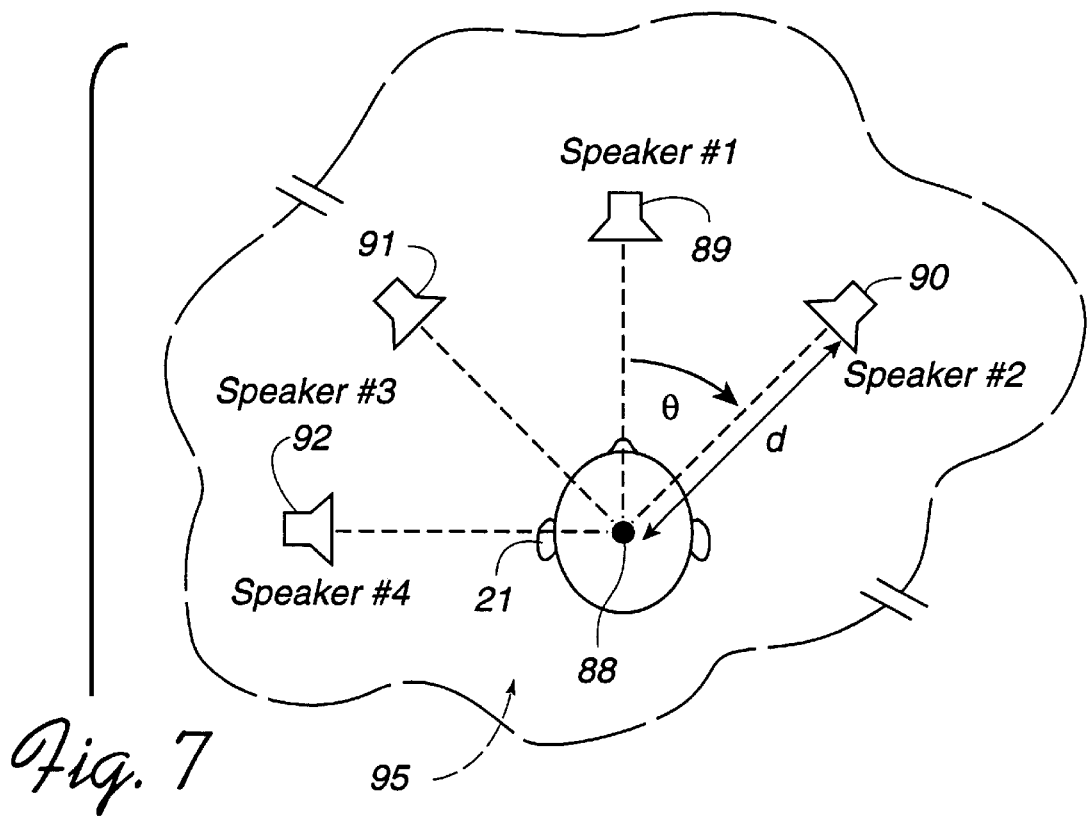
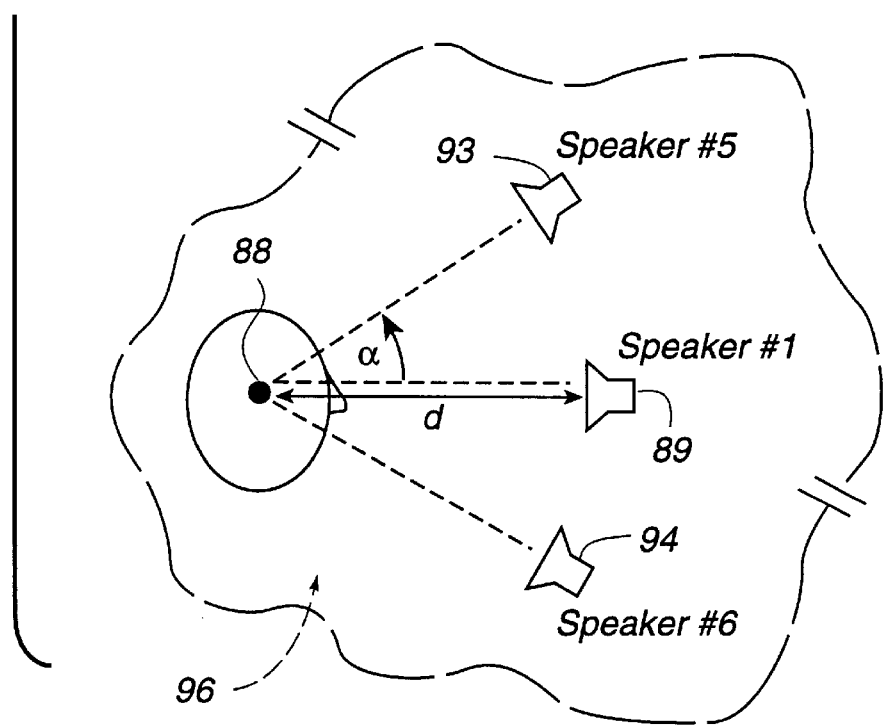
Fig. 7

FINISH THIS

VIRTUAL ELECTROACOUSTIC AUDIOMETRY FOR UNAIDED SIMULATED AIDED, AND AIDED HEARING EVALUATION

This is a continuation of application Ser. No. 08/292,073 filed Aug. 17, 1994, now abandoned.

BACKGROUND OF THE INVENTION

1. Technical Field

The present invention relates to hearing evaluation and hearing aid fitting. More particularly, the present invention relates to virtual electroacoustic audiometry for unaided, simulated aided, and aided hearing evaluation.

2. Description of the Prior Art

The human auditory system processes sounds from a complex three-dimensional space via the external, middle, and inner ear, as well as via the complex neural pathways that lead to the auditory cortex within the brain. A measurable hearing loss, due to various conductive, sensorineural, or central auditory disorders, affects a significant percentage of the human population, particularly elderly persons. Rehabilitation via hearing aids remains the only viable option for those types of hearing impairments that cannot otherwise be medically treated or surgically alleviated.

Advances in hearing aids and fitting technologies are continuously being made. Today's ear-level hearing aids, i.e. in-the-ear (ITE), behind-the-ear (BTE), in-the-canal (ITC), and completely-in-the-canal (CIC) types, are more cosmetically appealing due to improvements in electronic and mechanical miniaturization. More significant, however, is the increasing availability of advanced hearing aid signal processing schemes, such as adaptive filtering and multi-band dynamic compression.

As manufacturers are continuously developing new hearing aids with unique signal processing schemes, a hearing aid dispensing professional is faced with the increasingly difficult task of prescribing and selecting a hearing aid for a hearing-impaired individual from the available selection. A cursory look at available hearing aid processing schemes reveals an impressive array of categories, sub-categories, and associated acronyms that are baffling to most hearing aid dispensing professionals (see Mueller, H. G., *A Practical Guide To Today's Bonanza of Underused High-Tech Hearing Products*, The Hearing Journal, vol. 46, no. 3, pp. 13–27, 1993).

Today, optimal fitting of prescription hearing aids remains an elusive goal in auditory rehabilitation. The fundamental problem is that there are numerous electrical, acoustic, physical, and other parameters that affect hearing aid performance. These parameters include signal processing schemes, electronic circuit adjustments, size of hearing aid, insertion depth, venting size, patient controls, and life-style related factors that must be considered when prescribing and fitting a hearing aid. These hearing aid parameters are not only complex and highly interrelated, but also vary according to the unique interaction of the hearing device with the hearing-impaired individual.

Generally, the in situ performance characteristics of a hearing aid cannot be predicted with today's conventional fitting instrumentation and methods. Dissatisfaction among hearing aid user's, partially due to poor hearing aid prescription fitting, is manifested by a high return rates, often exceeding 20% according to industry reports.

Factors that Contribute to Unsatisfactory Hearing Aid Results

I. Inaccuracy of conventional diagnostic audiometry

Assessment of hearing is the first step in the prescribing and fitting of a hearing aid. Accurate assessment of the individual's hearing function is important because all hearing aid prescriptive formulas depend on one or more sets of hearing diagnostic data (see Mueller, H. G., Hawkins, D. B., Northern, J. L., *Probe Microphone Measurements: Hearing Aid Selection and Assessment*, Singular Publishing Group, Inc., 1992: Ch. 5).

The hearing aid prescription process involves translating the diagnostic data into target hearing aid electroacoustic parameters that are used in the selection of the hearing aid. Traditional hearing evaluation methods and instruments employ a variety of air-conduction transducers for coupling acoustic signals into the ear. Commonly used transducers include supra-aural earphones, such as TDH-39, TDH-49, TDH-50, insert earphones, such as ER-3A, and free-field speakers (see *Specification of Audiometers*, ANSI-S3.6-1989, American Standards National Institute).

A threshold measurement obtained with such transducers is referenced to a mean threshold obtained by testing a group of otologically normal individuals. This mean threshold, by definition, is referred to as the zero decibel hearing-level or 0 dB HL. With this zero reference concept, threshold measurements of otologically normal persons can vary by 20 dB or more. These variations can be attributed to following factors:

1. Variability due to transducer type used and placement with respect to the ear.

In a study by Mowrer, et al discrepancies of 10 dB were found in 36% of threshold measurements (see Mowrer, D. E., Stearns, C., *Threshold measurement variability among hearing aid dispensers*, Hearing Instrument, vol. 43, No. 4, 1992). Another major disadvantage of measurements obtained using a traditional transducer is that results are not interchangeable with measurements taken with another transducer for a given individual (see Gauthier, E. A., Rapisadri, D. A., *A Threshold is a Threshold is a Threshold . . . or is it?*, Hearing Instruments, vol. 43, no. 3, 1992).

2. Variability due to transducer calibration methods that employ couplers that do not represent the human ear.

Although recently developed couplers more closely match the acoustic impedance characteristics of an average human ear, there is still disagreement as to the accuracy of this artificial ear (see Katz, J., *Handbook of Clinical Audiology*, Third Edition, 1985, pp. 126). Most calibration methods today rely on 6-cc or 2-cc couplers that are known to have considerable acoustic characteristic discrepancies from real human ears (see *Specification of Audiometers*, ANSI-S3.6-1989, American Standards National Institute). Furthermore, even if an agreement was made regarding an average artificial ear, variability among individuals is significant due to individual acoustic characteristics of pinna, ear canal, concha, and to a lesser extent, the head, and the torso (see Mueller, H. G., Hawkins, D. B., Northern, J. L., *Probe Microphone Measurements: Hearing Aid Selection and Assessment*, 1992, pp. 49–50). In one study, inter-subject variability was up to 38 dB across six standard audiometric frequencies when sound pressure levels (SPL) were measured at the tympanic membrane for 50 ears of 25 adults (see Valente, M., Potts, L., Valente, M., Vass, B., *Intersubject Variability of Real-Ear SPL:TDH-39P vs ER-3A Earphones*, In press, JASA).

3. Conventional audiometric measurement methods do not provide a means of self-calibration even though transducer characteristics are known for changes due to wear or damage of the moving diaphragm.

Clinicians who use regular subjective listening methods simply cannot detect gradual changes in transducer sensitivity.

Although errors due to the above factors are not likely to be accumulative in all cases, the potential for substantial errors is always present. Furthermore, these errors are not consistent across all frequencies and therefore cannot be simply compensated for during the fitting process via an overall volume adjustment.

II. Lack of realistic listening conditions in the unaided and aided hearing assessment 1. Lack of Binaural Advantage Considerations.

Many studies have demonstrated the advantage of binaural versus monaural listening (see Cherry, E. C., *Some Experiments on the Recognition of Speech with One and Two Ears*, JASA, vol. 25, no. 5, 1953, pp. 975–979; Cherry, E. C., and Tylor, W, K., *Some Further Experiments on the Recognition of Speech with One and Two Ears*, JASA, vol. 26, 1954, pp. 549–554). These studies have focused on the advantages offered by the Binaural Masking Level Difference (BMLD) and Binaural Intelligibility Level Difference (BILD).

Early studies of BMLD and BILD involved the presentation of signal and noise to one or both ears at various phase relationships. Tone detection and speech intelligibility were shown to vary as much as 15 dB, depending on the signal/noise phase relationship. Even though many of these studies suggest the significance of binaural considerations, today's hearing assessment methods, unaided and aided, primarily deal with monaural test conditions, i.e. testing one ear at a time.

2. Lack of Spatialized Sound Considerations.

When audiometric signals such as speech and/or noise are delivered to the ear via a conventional audiometers and associated transducers, the sound perception by the test subject is not localized to any particular point in space (see *Specification of Audiometers*, ANSI-S3.6-1989, American Standards National Institute). For example, in speech audiometry evaluation, the speech stimuli level is adjusted for one ear and speech noise level is separately adjusted in the opposite ear. The test subject perceives sounds to be within the head and localization is limited to left/right direction. This type of signal presentation and perception is referred to as intracranial and is unlike the way humans normally perceive natural sounds. Recent studies by Bronkhorst and Plomp, and Begault expanded on previous binaural interaction advantage studies by employing headphone localization techniques (see Bronkhorst, A. W., Plomp, R., *The Effects of Head-Induced Interaural Time and Level Differences on Speech Intelligibility in Noise*, Journal of the Acoustical Society of America, vol. 83, no. 4, 1988, pp. 1508–1516; Bronkhorst, A. W.; Plomp, R., *The Effects of Multiple Speech-like Maskers on Binaural Speech Recognition in Normal and Impaired Hearing*, Journal of the Acoustical Society of America, vol. vol. 92, no. 6, 1992, pp. 3132–3139; and Bagault, D. R., *Call Sign Intelligibility Improvement Using a Spatial Auditory Display*, Ames Research Center, NASA Technical Memorandum 104014, April 1993). The results of these studies conclude the speech perception is not only dependent on intensity levels but also on the spatial relationship between speech and noise.

3. Lack of Evaluation Methods in Realistic Listening Environments.

Speech intelligibility and discrimination deteriorates in the presence of competing speech and other environmental sounds. Furthermore, the acoustic properties of a room, e.g. its walls and objects within the room, all play an important role in the filtering process subjected to the original signal source. These filtering effects are especially significant for hearing-impaired individuals who typically have a limited frequency response and dynamic range in their hearing function.

Today's methods of presenting competing and environmental sounds via conventional transducers fail to represent the acoustic reality of the typical listening condition. Recorded sound material presented via tape players, compact disks, or computer digital playback are subject to filtering effects of the transducer employed and/or the room acoustics of the clinical setup. There are no hearing assessment methods today that can evaluate or predict the hearing performance of an individual in a specific and realistic listening scenario.

For example, the hearing performance of a hearing-impaired child in a typical classroom in the unaided condition, and the hearing performance of the child with a specific hearing aid, i.e. aided hearing, in the same classroom environment. These and other auditory experiences are presently considered a fact of life that can not be dealt with in a clinical setup (see Mueller, H. G., Hawkins, D. B., Northern, J. L, *Probe Microphone Measurements: Hearing Aid Selection and Assessment*, 1992, pp. 69).

III. Limitations of current real-ear measurement (REM) equipment and methods

In recent years, real ear measurement (REM) systems were developed to assess the in situ performance of a hearing aid. REM consists of test probe measurements of the ear response to free field stimulus, i.e. speakers, taken at the tympanic membrane. A secondary reference microphone is typically placed outside the ear canal close to the ear canal opening. The reference microphone is used to calibrate the test probe as well as to regulate the stimulus level as the head moves with respect to the free field speaker.

For a comprehensive REM evaluation, measurement of the real ear response for the unaided, i.e. open canal, condition is first taken. Target hearing aid characteristics are then calculated based on the natural ear canal response characteristics, as well as other criteria (see Mueller, H. G., Hawkins, D. B., Northern, J. L., *Probe Microphone Measurements: Hearing Aid Selection and Assessment*, 1992, Ch. 5). When the hearing aid is prescribed, ordered, and received during a subsequent visit, the aid is inserted over the probe tube and adjusted to match the prescribed target hearing aid characteristics.

REM evaluation and REM-based prescriptive methods provide considerable improvements over previous fitting methods which relied on the combination of audiometric data and hearing aid 2-cc coupler specifications. Although REM offers insight into the in situ performance of the hearing aid, it suffers from several fundamental problems, as described below:

1. REM test results vary considerably depending on speaker position/orientation with respect to the ear, particularly at higher frequencies (see Mueller, H. G., Hawkins, D. B., Northern, J. L., *Probe Microphone Measurements: Hearing Aid Selection and Assessment*, 1992, pp. 72–74).

2. Real ear measurements are taken with a specific stimulus type, source-ear distance/orientation, and room acoustics. The specific test condition may not represent realistic listening scenarios encountered by hearing aid users. In fact, using conventional REM approaches, a hearing aid may be optimized for a specific listening condition while compromising the performance under other conditions that may be more important to the hearing-impaired individual.

3. Accurate REMs require careful placement of the test probe within the ear canal of an individual. The closer the probe to the tympanic membrane, the more accurate the results are, particularly for high frequency measurements (see Mueller, H. G., Hawkins, D. B., Northern, J. L., *Probe Microphone Measurements: Hearing Aid Selection and Assessment*, 1992, pp. 74–79).

Present methods of probe placement are highly dependent on the operating clinician's skill and the specific length of the canal, which is about 25 mm for the average adult. Today's REM methods rely on visual observation of the probe tip. This is especially problematic when a hearing aid is placed in the canal during the aided evaluation process. The only exception to the conventional visual method is the acoustic response method developed by Nicolet Corp. for use in the Aurora system (see Chan, J., Geisler, C., *Estimation of Eardrum Acoustic Pressure and Ear Canal Length from Remote Points in the Canal*, J. Acoust. Soc. Am. 87 (3), March 1990, pp. 1237–1247; and U.S. Pat. No. 4,809,708, *Method and Apparatus for Real Ear Measurements*, March 1989). However, Nicolet's acoustic response method requires two calibration measurements prior to placement of the probe at the desired position within the ear canal.

4. REM test results vary considerably depending on the placement of the reference microphone near the ear. The errors are especially significant at frequencies of 6 kHz and higher (see Mueller, H. G., Hawkins, D. B., Northern, J. L., *Probe Microphone Measurements: Hearing Aid Selection and Assessment*, 1992, pp. 72–74).

5. REM instruments employ sound field speakers in a room with ambient background noise that often exceeds 50 dB SPL across standard audiometric frequencies. This necessitates stimulus levels of 60 dB or higher to produce measurements having sufficient signal-to-noise ratios. This is problematic if hearing aid performance characterization under low level acoustic stimuli is required.

IV. The problem of correlating diagnostic, prescription formulae, and real ear measurements A significant factor that contributes to the results of a hearing aid fitting is the problem of adequately correlating diagnostic data with fitting needs of the hearing-impaired individual. Diagnostic measurements are typically taken in dB HL with transducers that are calibrated in 6-cc couplers. Hearing aid specification and performance measurements employ 2-cc couplers which do not represent the real-ear. Fitting involves the use of one of several prescriptive formulae, with results that are known to vary as much as 15 dB for the same diagnostic data across standard audiometric frequencies (see Mueller, H. G., Hawkins, D. B., Northern, J. L., *Probe Microphone Measurements: Hearing Aid Selection and Assessment*, 1992, p 107). These fitting formulae incorporate statistically based conversion factors that simplify the correlation of hearing aid requirements to a particular hearing impairment. However, averaged conversion factors are known to vary considerably with respect to objectively measured individual conversion factors.

Several methods and protocols have been suggested to alleviate errors associated with measurement errors and data correlation (see Sandberg, R., McSpaden, J., Allen, D., *Real Measurement from Real Ear Equipment. Hearing Instruments*, Vol. 42, No. 3, 1991, pp. 17–18). However, many of these protocols have not yet been widely accepted due to limitations of conventional audiometry and Real-Ear Measurement (REM) equipment and other factors related to efficiency of the proposed protocols in clinical setups.

Hearing rehabilitation through the use of hearing aids remains the only viable option for many hearing impaired individuals who cannot be medically or otherwise treated. A full audiometric evaluation is a required first step prior to fitting a hearing aid. Pure tones and one or more speech perception tests are typically involved in the basic audiometric test battery. Suprathreshold measurements may also be taken to establish a hearing dynamic range profile, in addition to the frequency response profile obtained in the threshold audiogram test. Following the audiometric evaluation, a hearing aid is then prescribed, selected, ordered, and subsequently tried and adjusted after being received from the manufacturer or assembled in the clinic. The fitting or determination of the electroacoustic parameters of a hearing aid typically involve a combination of objective measurements to achieve a desired target characteristics based on one of many prescriptive formulae and subjective measures based on the individual's subjective response to speech and other sounds at various loudness levels.

Conventional audiometry methods, employing headphones, inserts, or sound-field speakers, rely on presenting acoustic energy to the ear of the individual in a manner which is not representative of sound delivery under realistic listening conditions. Conventional audiometers present various tones, speech, and noise stimuli to each ear individually and thus are not capable of investigating the individual's binaural integration advantage, or of assessing the hearing function in a three-dimensional sound environment.

Another major disadvantage of conventional audiometry methods is the inability of such methods to assess accurately and objectively, in absolute physical terms such as dB SPL, the hearing function of an individual with respect to the inside of the ear canal to correlate unaided evaluation results to hearing aid requirements. One exception is the probe-mike-calibrated fitting system developed by Ensoniq, which only addresses testing accuracy (see Gauthier, E. A., Rapisadri, D. A., *A Threshold is a Threshold is a Threshold . . . or is it?: Hearing Instruments*, vol. 43, no. 3, 1992).

Furthermore, conventional audiometry instruments and methods are not capable of simulating the electroacoustic performance of one or more prescribed hearing aids and assessing their simulated function in realistic acoustic conditions relevant to the individual's unique listening requirements.

The master hearing aid concept, which gained some popularity in the '70s and '80s, involves an instrument that presents simulated hearing aids to the hearing aid user (see *Selection Instrumentation/Master Hearing Aids in Review*, Hearing Instruments, Vol. 39, No. 3, 1988). Veroba et al (U.S. Pat. No. 4,759,070, *Patient Controlled Master Hearing Aid*, Jul. 19, 1988) describe a patient controlled hearing aid module that is inserted into the ear canal and connected to a test module which offers multiple signal processing options, e.g. analog circuit blocks, to the individual. Hearing aid characteristics are determined by a tournament process of elimination, while the hearing-impaired person is presented with real-world sounds played back from tape decks via a set of speakers located around the hearing-impaired person's head. The system's fitting process is based on subjective responses of the hearing-impaired who must continuously decide on an alternative signal processing option, and supposedly eventually arrive at an optimal fitting.

The fitting process via the Veroba system, commercially known as the Programmable Auditory Comparator, an essentially obsolete product, does not involve any objective measurements or calculations for selecting and fitting of the hearing aid. In fact, the entire fitting process is based on the subjective response of the hearing impaired person. Clearly, most hearing impaired individuals, on their own, cannot explore in a timely and efficient manner the spectrum of various complex and interrelated electroacoustic parameters of a hearing aid under various listening environments. A serious limitation of Veroba is that it does not teach how to assess objectively the performance of the simulated hearing aid, nor does it teach how the aided performance is related to the individual's unaided response determined previously during the audiometric evaluation process.

A major unsubstantiated claim in Veroba's system is the simulation of a realistic acoustical environment via tape-deck playback and speakers located around the head of the hearing-impaired individual. However, recorded acoustic signals that are played back are further subjected to acoustic modifications due to speaker characteristics, speaker position with respect to ear/head, and acoustic characteristics of the room, i.e. wall reflections and acoustic absorption. Without factoring in all of the specific acoustic modifiers in the transmission channel between the tape-deck and the individual's ear, a realistic listening condition cannot be achieved with Veroba or any such system. Furthermore, Veroba is not capable of manipulating the acoustic condition from its recorded form, e.g. by projecting an audio source in a specific location within a three-dimensional acoustic space with a specific acoustic boundary condition.

Another hearing aid simulator, the ITS-hearing aid simulator developed by Breakthrough, Inc. offers computer digital audio playback of digital recordings obtained from the output of various hearing aids (see *ITS-Hearing Aid Simulator*, Product brochure, Breakthrough, Inc., 1993). Each recording segment represents a specific acoustic input, listening scenario, hearing aid model, and hearing aid electroacoustic setting. The recording segments require memory space either on a hard disk or other known forms of memory storage devices, such as compact-disk read-only-memory. This digital-recording-based approach renders impractical the arbitrary selection of a hearing aid, hearing aid setting, and input stimulus for a hearing-impaired individual, when considering all the possible combinations. Furthermore, the effects of hearing aid vent sizes, and associated occlusion effect, insertion depth, and individual external ears, cannot be simulated with the proposed hearing aid simulator because it relies on conventional transducers, i.e. headphones and insert earphones.

For similar reasons, many other commercially available master hearing aid systems, do not have the ability to simulate accurately a hearing aid in a realistic listening environment. Furthermore, these systems do not include objective measurement methods for evaluating simulated aided versus unaided conditions. For these and other reasons, virtually all dispensed hearing aids today are fitted without the use of master hearing aid or hearing aid simulator instruments.

State-of-the-art REM equipment allows for in-the-ear-canal acoustic response measurements. The acoustic stimuli are typically generated by the REM equipment itself and delivered via a speaker, typically positioned at 0° azimuth, or with two speakers positioned at 45° azimuth, with the respect to the transverse plane of the head. The response measurements, i.e. free-field to real-ear transfer function, are essentially one-dimensional since they only provide a single transfer function per ear in a particular speaker-ear relationship, and are thus not capable of establishing a multi-dimensional profile of the real-ear response. Another disadvantage of conventional REM equipment and methods is the lack of real speech stimuli presentation because most REM equipment only offer pure-tone, pure-tone sweep, speech-noise and other speech-like stimuli. These stimuli do not explore responses to particular speech segments that may be important to the hearing-impaired individual during unaided and aided conditions.

Recent developments relating to electroacoustic hearing aid measures involve the testing of hearing aids in more realistic conditions. Real speech signals instead of pure tones and speech-like noise signals were employed in a recommended test protocol; and spectrogram plots indicating temporal, i.e. time, analysis of the acoustic energy in dB SPL versus frequency was compared for hearing aid input versus output (see Jamieson, D., *Consumer-Based Electroacoustic Hearing Aid Measures*, JSLPA Suppl. 1, January 1993). The limitations of the proposed protocol include: limited acoustic reality due to the specified sound delivery method via a speaker to a hearing aid in an enclosed chamber; and limited value of the spectrogram plots which do not directly indicate the relationship of the plot to audibility and loudness discomfort.

Other recent developments involve three-dimensional sound presentation via headphone transducers (see Wightman, F. L., Kistler, D. J., *Headphone Simulation of Free-Field Listening. I: Stimulus Synthesis*, JASA. vol. 85, no. 2, 1989, pp. 858–867; and Wightman, F. L., Kistler, D. J., *Headphone Simulation of Free-Field Listening. II: Psychophysical Validation*, JASA. vol. 85, no. 2, 1989, pp. 868–878). These three-dimensional effects are achieved by recreating the in-the-ear-canal acoustic response to free-field signals via headphones or speakers (see U.S. Pat. No. 4,118,599, *Stereophonic Sound Reproduction System*, Oct. 3, 1978; U.S. Pat. No. 4,219,696, *Sound Image Localization Control System*, Aug. 26, 1980; U.S. Pat. No. 5,173,944, *Head Related Transfer Function Pseudo-Stereophony*, Dec. 22, 1992; U.S. Pat. No. 4,139,728, *Signal Processing Circuit*, Feb. 13, 1979; and U.S. Pat. No. 4,774,515, *Altitude Indicator*, Sep. 27, 1988). This involves digital filtering of source signals based on head-related-transfer-function (HRTF). The HRTF, essentially real-ear unaided response (REUR) in three-dimensional space, is a frequency dependent amplitude and time delay measurement that results from head shadowing, pinna, concha, and ear canals. The HRTF enables externalization of localized sound with headphones. Source signals that are processed with HRTF provide the listener with free-field listening experience according to the controls of the signal processing parameters.

Present research and development efforts in three-dimensional audio is mainly focused on commercial musical recordings, playback enhancement, and human-machine interface enhancement (see Bagault, D. R., *Call Sign Intelligibility Improvement Using a Spatial Auditory Disaply*, Ames Research Center, NASA Technical Memorandum 104014, April 1993; and Begault, D., Wenzel, E., *Headphone Localization of Speech*, Human Factors, 25 (2), pp. 361–376, 1993) and virtual reality systems (see *The Beachtron-Three-dimensional audio for PC-compatibles*, reference manual, Crystal River Engineering, Inc., Revision D, November, 1993). The object of these three-dimensional audio systems has been limited to simulating situational awareness in an approximate virtual acoustic environment since non-individualized HRTF set is typically employed.

The application of three-dimensional audio in objective in-the-ear-canal assessment of hearing in the unaided, simulated aided, and aided conditions would be a significant and extremely helpful departure from known audiometric techniques.

SUMMARY OF THE INVENTION

The invention provides a virtual electroacoustic audiometer (VEA), which is a system used in the assessment of human hearing function in the unaided, simulated aided, and aided conditions. A pair of intra-canal prostheses (ICP) are placed in the two ear canals of an individual to deliver acoustic stimuli. A probe measurement system, partially inserted in the ICP, measures the in-the-ear-canal response conditions near the tympanic membrane during all hearing evaluation, thus providing a common reference point for correlating responses in the unaided, simulated aided, and aided evaluation conditions. A unique modular hearing aid defined in accordance with the results of such hearing assessment is also provided that includes highly configurable electroacoustic and electronic signal processing elements.

During unaided evaluation, the system performs audiometric tests, such as pure tone thresholds, uncomfortable loudness levels (UCL), speech reception threshold, and speech discrimination. These peripheral hearing tests, as well as other central auditory processing (CAP) tests, evaluate the hearing function of the human in response to acoustic stimuli measured near the tympanic membrane in absolute sound pressure level (SPL) terms, unlike conventional stimuli which are presented in relative hearing level (HL) terms.

Another significant feature of the VEA is its ability to synthesize, or create, acoustic signals that are representative of signals received in real listening environments in a three-dimensional space. This is achieved by incorporating the various filtering effects of room acoustics, atmospheric absorption, spreading loss, interaural delay, and spectral shaping of external ear, and other body effects. For example, a listening condition representing a teacher-talker in classroom is digitally synthesized and acoustically delivered via the ICP to a child to assess his/her unaided and aided listening ability in a classroom environment. Spatialized competing signals representing school children noise is optionally presented in addition to the spatialized primary speech signal, i.e. the teacher, to assess further the child's speech discrimination ability in the presence of background noise.

The unaided evaluation method involves both ears in the listening experience similar to the way humans normally hear sounds, with each ear receiving a portion of the acoustic energy according to the relationship between each ear and the various virtual audio sources. In contrast, conventional audiometry methods present intracranial acoustic stimuli to each ear individually, for example, speech to one ear, and competing noise in the opposite ear.

The simulated aided assessment of the VEA system is accomplished by incorporating the electroacoustic performance of a desired hearing aid into the unaided digital synthesis of acoustic signals. The simulated hearing aid electroacoustic parameters include microphone and receiver transfer functions, and amplifier and filter characteristics.

Specific or generalized acoustic models are digitally presented to the input of the simulated hearing aid process. Specific acoustic models represent listening scenarios that are important to the individual under evaluation and that may be selected and manipulated by the operating clinician, for example a teacher-talker source model in a classroom environment model with a specific source-ear relationship. A typical goal in such a specific scenario is to maximize speech intelligibility by optimizing the electroacoustic characteristics of the simulated hearing aid. Generalized acoustic conditions represent listening scenarios that are associated with normative response data. An example of a generalized model is an audiologic word list, such as W-22, having a specific spatialized background noise. Test scores are compared with general model normative data stored in the system's memory.

The VEA system also simulates other hearing aid effects that can not be simulated by the digital synthesis process due to the unique effects of the individual ear. These include the occlusion effect, venting size, and oscillatory feedback potential. The occlusion effect is a phenomenon that results in changes to the perceived characteristics of the individual's own voice when the ear canal is occluded with a hearing aid.

In addition, the VEA system offers a method of measuring various individualized acoustic transfer functions in a three-dimensional space, which are incorporated during the various synthesis processes to create virtual acoustic conditions for an individual.

BRIEF DESCRIPTION OF THE DRAWINGS

FIG. 7 is a schematic diagram showing speaker arrangement in a virtual acoustic space measurement system, including transverse plane speakers, and sagittal plane speakers according to the invention;

DETAILED DESCRIPTION OF THE INVENTION

For purposes of the description herein, the following definitions shall be consistently applied:

Window: Refers to a graphical area displayed on a computer screen, that represents a collection of controls, objects, entry fields, and plots, that are grouped together according to a logical functional manner.

Iconized: Refers to an active window that is shown as an icon. Its display is disabled but may be enabled by clicking on the icon on the computer screen.

The virtual electroacoustic audiometer (VEA) described herein is a unitary instrument that is used in the hearing assessment in the unaided, simulated aided, and aided conditions. The VEA also offers new methods for hearing aid fitting and analysis using a combination of digital synthesis of realistic acoustic stimuli and in-the-ear-canal response measurements throughout the assessment and fitting processes.

Figure 1:
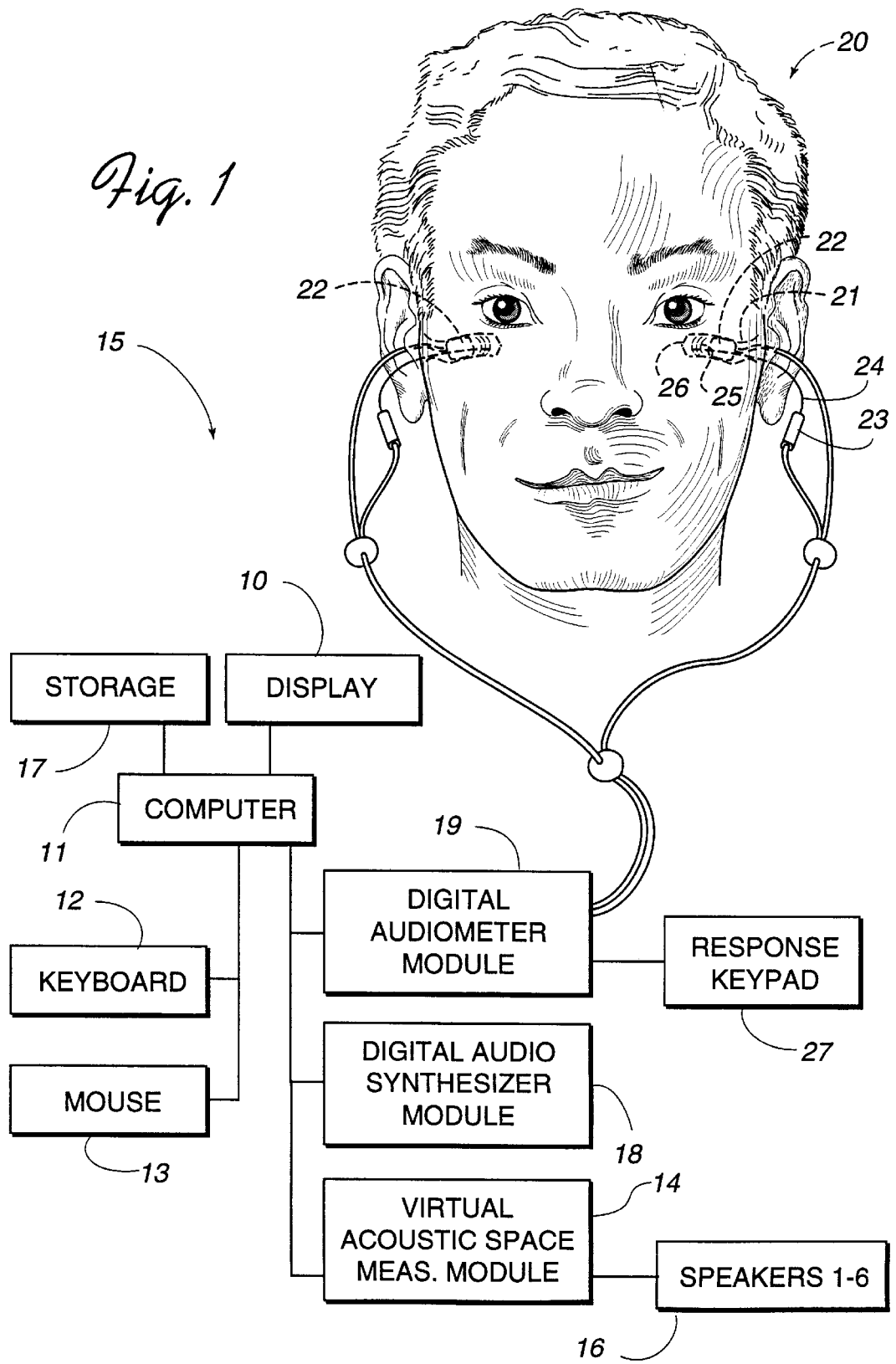
FIG. 1 is a block level schematic diagram showing the major components of the VEA system, including dual ICP prostheses inserted in the ear canal of an individual; a probe microphone system; and a computer system including a digital audio synthesizer module, a digital audiometer module, and a virtual acoustic space measurement module according to the invention.

FIG. 1 shows the main components of the preferred embodiment of the VEA system 15. A pair of intra-canal prostheses (ICP) 22 is inserted in the ear canal 21 of an individual for delivering acoustic stimuli 25 in a manner similar to that of a hearing aid. Each ICP contains a receiver, i.e. a speaker, for transmitting acoustic signals to the tympanic membrane 26. The ICP also contains a probe tube 24 for measuring the acoustic response that results from the unique interaction of the receiver-produced acoustic stimuli and the ear-canal characteristics of the individual. A probe microphone system consisting of a probe tube 24 and probe microphone 23 measures acoustic signals from the ear canal 21 and provides electrical signals representative of the acoustic signals. A response keyboard 27 is provided to register a response from the test subject 20 during various hearing evaluation tests.

Each ICP receiver 22 is electrically connected to a digital audiometer module 19 that provides an interface to various audiometric transducers including the ICP receiver 22 and probe measurement system 23. The digital audiometer module is connected to a digital audio synthesizer module 18 and a virtual acoustic space measurement module 14 via various inter-module cables. The virtual acoustic space measurement module includes an output terminal 16 for connection to a plurality of test speakers. These modules may be contained at or within a standard personal computer (PC) 11 that also contains standard computer accessories such as memory storage devices 17, a display monitor 10, a keyboard 12, and a mouse 13. Memory storage devices are collectively referred to as system memory 17.

Figure 2:
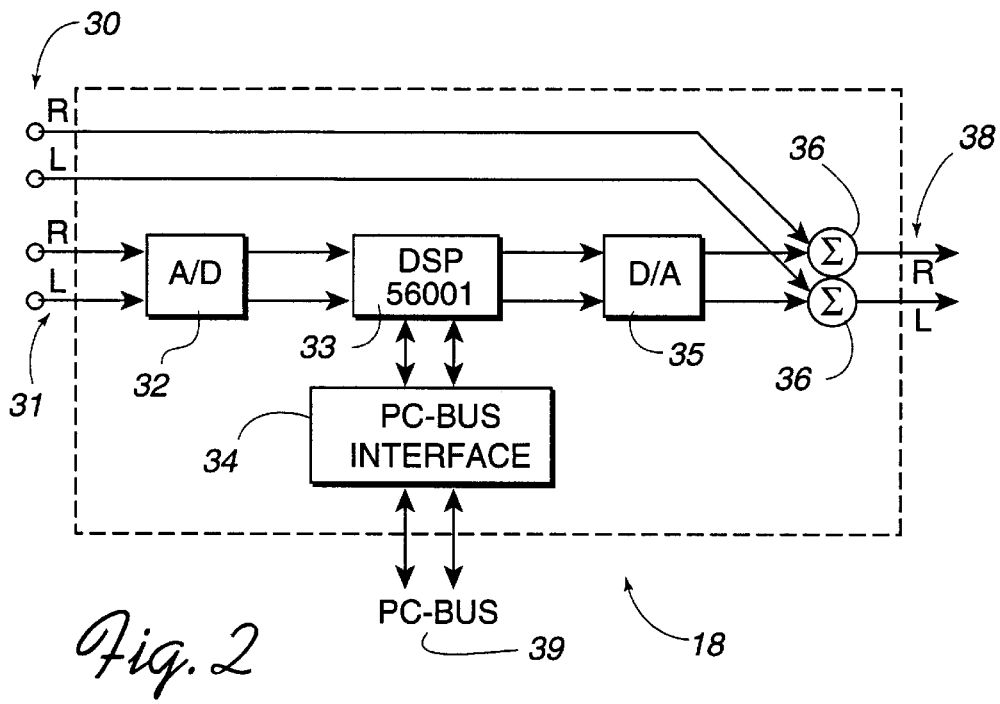
FIG. 2 is a block level schematic diagram of a digital audio synthesizer module according to the invention.
Figure 4:
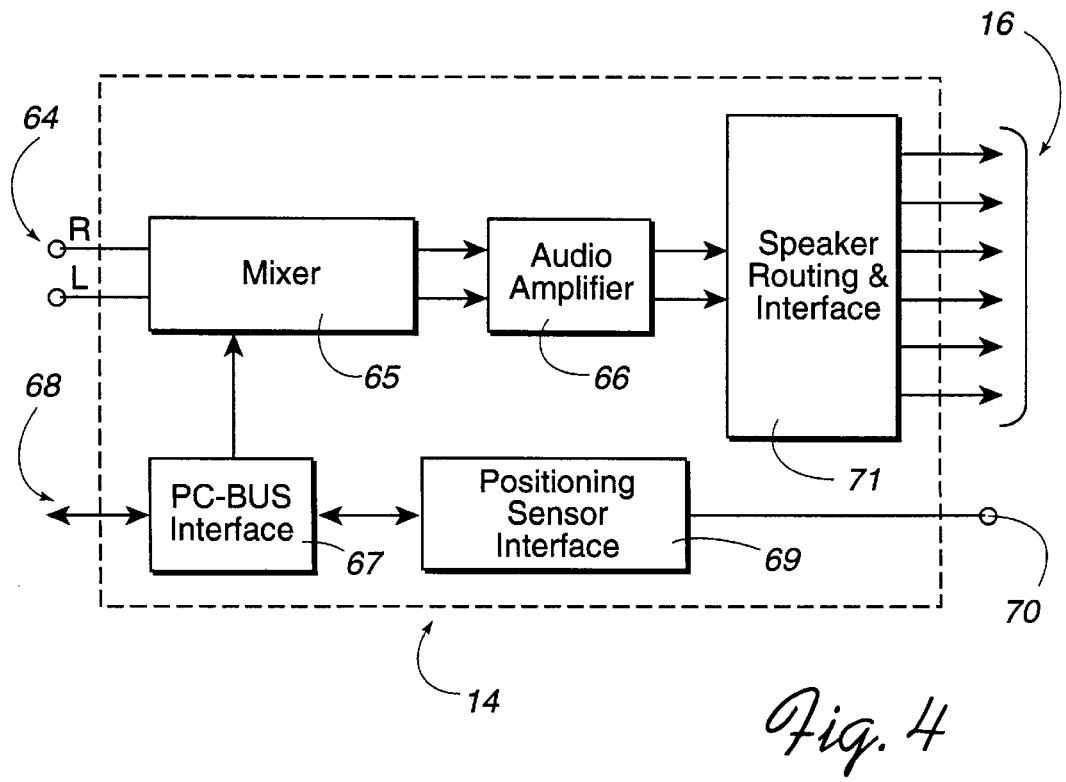
FIG. 4 is a block level schematic diagram of a virtual acoustic space measurement module according to the invention.
Figure 3:
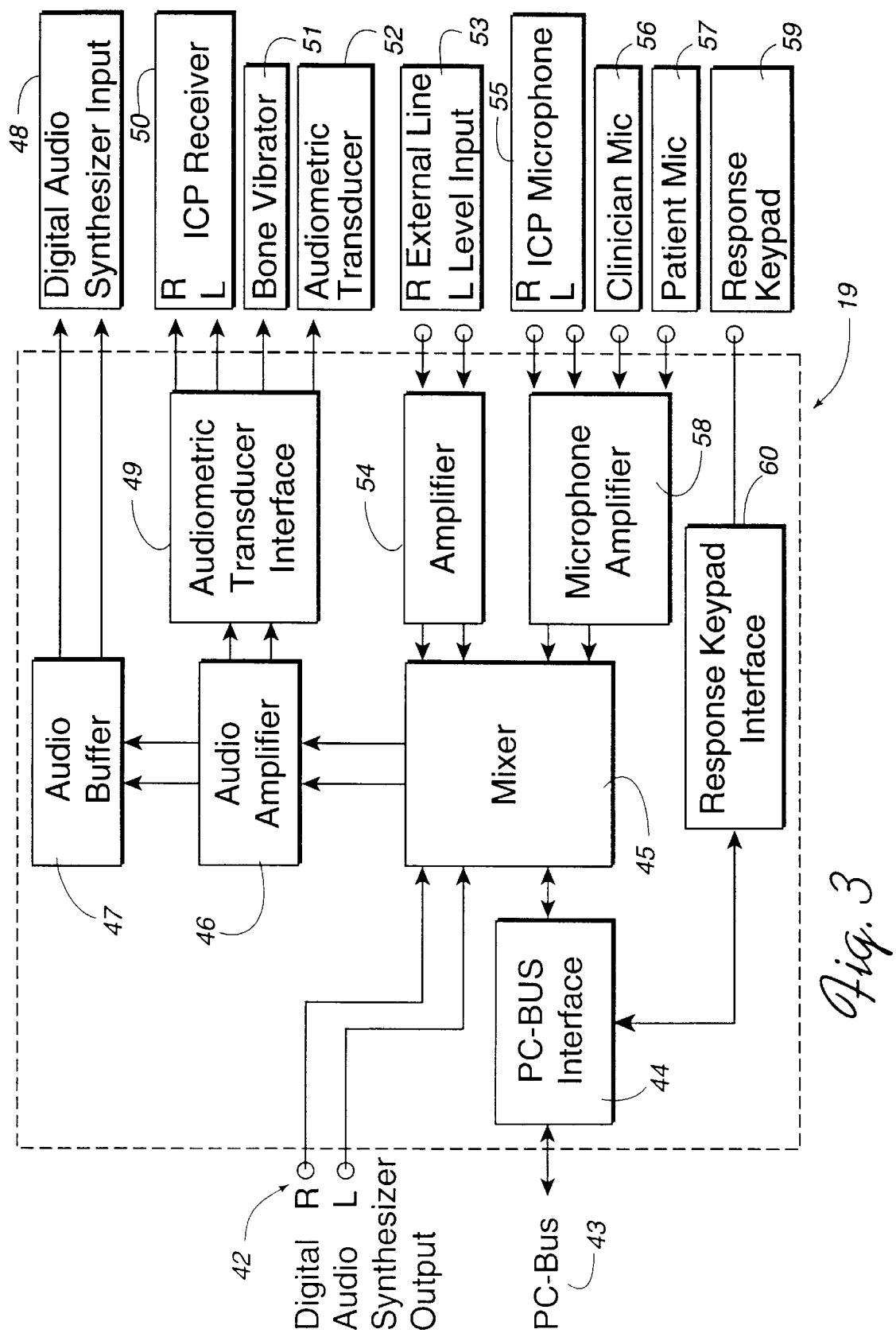
FIG. 3 is a block level schematic diagram of a digital audiometer module according to the invention.

Block diagrams of the digital audio synthesizer, digital audiometer and virtual acoustic space measurement modules are shown in FIGS. 2, 3, and 4.

In the exemplary embodiment of the invention, the digital audio synthesizer, digital audiometer, and virtual acoustic space measurement modules are connected to the personal computer system via the Industry Standard Architecture (ISA)-bus interface 34 and ISA-bus 39 of the personal computer (see, for example FIG. 2). Digital data representing audio sources are retrieved from the system memory via the bus interface 34, and are digitally processed by a digital signal processor 33 within the digital audio synthesizer module 18. The digitally processed data are then converted to analog form using an digital-to-analog converter 35 that typically operates at conversion rate of 44.1 kHz, or at another rate depending on the desired signal bandwidth required.

The digital audio synthesizer module also receives analog signals representing audio signals via its input connector 31 from external audio sources such as tape or CD players (not shown). Received analog signals are converted to digital signals by the analog-to-digital converter 32 for signal processing via digital signal processor 33.

Multiple digital audio synthesizer modules (not shown) may be used to enhance the system's digital signal processing capability. This is particularly useful for parallel real-time binaural signal synthesis. Multiple digital audio synthesizer modules are cascaded by connecting the output 38 of one digital audio synthesizer module to the auxiliary input 30, or input 31 of another digital audio synthesizer module. The internal and auxiliary signals are combined within the module at a summing node 36 prior to output. In the preferred embodiment of the invention, two digital audio synthesizer modules are used. Each module employs a Motorola DSP56001 digital signal processor clocked at 40 MHz.

The analog output 38 from the digital audio synthesizer module 18 is routed to the mixer 45 of the digital audiometer module 19 (FIG. 3) via a connector 42. Analog audio signals received at the digital audiometer module are mixed via mixer circuit 45, amplified via an audio amplifier circuit 46, and impedance matched and routed to various audiometric transducers via an audiometric transducer interface circuit 49. Outputs to audiometric transducers include ICPs 50 (discussed above, and in further detail below), bone vibrators 51, a headphone 52 (not shown), and other conventional methods of delivering sounds to the ear of an individual.

Amplified signals from the audio amplifier 46 are also sent to the digital audio synthesizer module input 31 from an audio buffer circuit 47 output connection 48. The mixer circuit 45 also includes connections for receiving audio signals from ICP microphones 55, an operating clinician microphone 56, and a patient microphone 57, via a microphone amplifier 58.

External line-level signals received at input connectors 53 are also amplified via an amplifier 54 and sent to mixer circuit 45. A response keypad interface circuit 60 is employed to interface the system to the response keypad via a connector 59 to register an individual's response to acoustic stimuli during various audiometric evaluation processes. The operating clinician microphone, connected to the digital audiometer module, allows the operating clinician to communicate with the patient via the ICP pair. The patient microphone allows the patient to communicate back to the operating clinician during certain audiometric tests that require verbal responses from the patient. The patient microphone is also used in occlusion effect measurements, as are described in more detail below.

The digital audiometer module also includes a PC-BUS connection 43 and PC-BUS interface circuit 44 that link the digital audiometer module to the VEA to coordinate module operation at the system level.

The VEA also includes a virtual acoustic space measurement system (FIG. 5) that is used to evaluate the individual's acoustic transfer function set. A block diagram of the virtual acoustic space measurement module 14 is shown in FIG. 4. The virtual acoustic space measurement module receives electrical signals, representing various acoustic signals, from the digital audio synthesizer module output connectors 38 via a set of input connectors 64. Input signal level adjustment and routing is accomplished via a mixer circuit 65, an audio amplifier circuit 66, and a speaker routing and interface circuit 71. The output of the virtual acoustic space measurement module is thence coupled to various test speakers in a speaker array 16.

The virtual acoustic space measurement module also includes a PC-BUS connection 68 and PC-BUS interface circuit 67 that link the virtual acoustic space measurement module to the VEA to coordinate module operation at the system level. Such coordination includes processing information indicative of patient head position connected to the module from a patient head positioning sensor via a connector 70 and a positioning sensor interface circuit 69.

Figure 6:
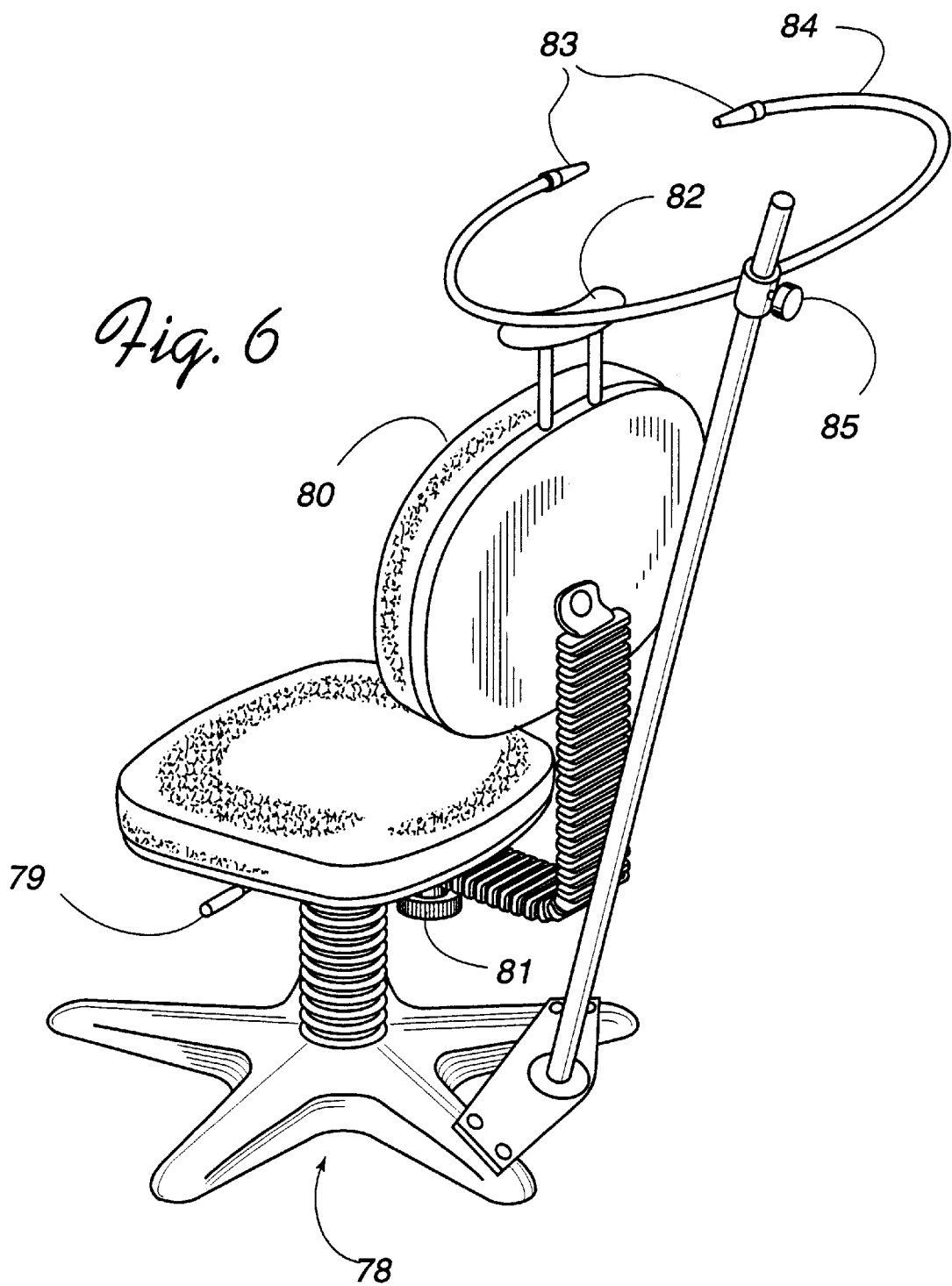
FIG. 6 is a perspective view of an adjustable chair used for positioning a patient's head during virtual acoustic space testing.

An adjustable chair 78 is preferably used to ensure proper ear positioning within the measurement space, as shown in FIG. 6. A vertical adjustment lever 79 adjusts the vertical position of the individual on the chair. A back adjustment knob 81 adjusts a chair back support 80. The head support 82 is adjustable to support the head of the individual seated on the chair. An ear position reference arm 84 provides a target reference by pointing a set of ear canal opening pointers 83 to the individual's ear canal openings. The ear position reference arm 84 is preferably removable from the ear area via a reference arm vertical adjustment knob 85 to minimize acoustic reflections into the ear area during transfer function measurements.

Figure 5:
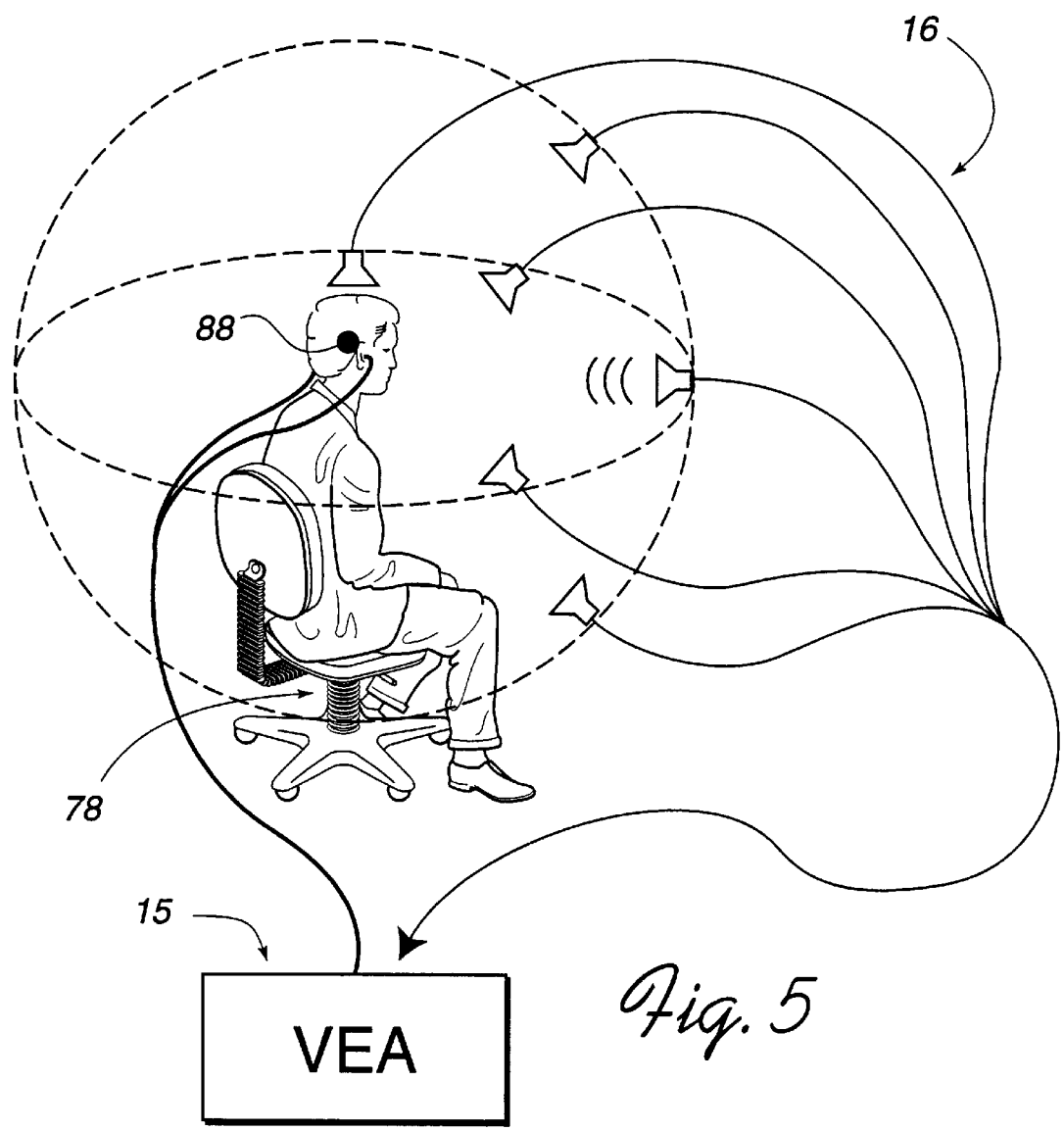
FIG. 5 is a block level schematic diagram of a virtual acoustic space measurement system according to the invention.

An infrared tracking method (not shown) may also be used to position and maintain the head in the proper position with respect to the speaker array 16, FIG. 5; 89–94, FIG. 7). A light-reflective target object (not shown) placed just below the ear lobe of the individual, may be used to reflect the infrared light from the incident infrared light emitter. Proper ear placement is indicated by reflected light which is detected by the positioning sensor interface 69 (FIG. 4).

The virtual acoustic space measurement system generates various sets of transfer functions that are used during the hearing evaluation process. Generally, a transfer function of a linear system defines a complex function H(jw) having magnitude and phase characteristics that are dependent on frequency (w). Once a transfer function H(jw) is determined, a system's response to an arbitrary input signal can be predicted or synthesized.

The transfer function set in the virtual acoustic space measurement system is obtained from a set of acoustic sources, such as speakers, positioned in a three-dimensional space. The preferred speaker setup is an array of six speakers 89–94 positioned at an equal distance (d) from a patient head reference point 88, as shown in FIGS. 5 and 7. The head reference point 88 is defined as the point bisecting the line joining the centers of the openings of the ear canal 21.

Four of the speakers, i.e. #1 (89), #2 (90), #3 (91), and #4 (92) are located in the transverse plane 95 containing the head reference point 88. Speakers 1 through 4 are positioned at azimuth angles 0°, 45°, 315°, and 270°, respectively, as shown in FIG. 7 at (step). Three of the speakers, i.e. #1 (89), #5 (93), and #6 (94) are located in the sagittal plane 96 containing the head reference point 88. Speakers #1, #5, and

6 are positioned at altitude angles of 0°, 45°, and −45°, respectively, as shown in FIG. 7 at B.

A set of transfer functions for the six-speaker configuration shown in FIG. 7 allows six pairs, i.e. right and left ear measurements, of frontal measurements where the head is facing speaker #1. An additional six pairs of back measurements are preferably taken where the head is facing opposite (not shown) to speaker #1. Accordingly, a complete transfer function set consists of 12 pairs of measurements that represent finite points in a sphere of a radius (d). Of the twelve paired measurements, eight paired measurements are in the transverse plane and six paired measurements are in the sagittal plane. Two paired measurements are common to both planes. Paired measurements contain not only individual transfer functions for each ear, but also contain the interaural phase relationship with respect to each speaker.

A transfer function measurement set with a pair of probes placed near the tympanic membrane in the unoccluded ear canal is referred to herein as the unaided transfer function $H_{ua}(p_n,jw)$, where $p_n$ is the location of speaker n defined by polar coordinates d, θ, and α, where d is the distance between the speaker and the head reference point as shown in FIG. 7 at A.; θ is the azimuth angle of sound incidence with the respect to transverse plane as shown in FIG. 7 at A.; and α is the altitude angle with respect to the sagittal plane as shown in FIG. 7 at B. $H_{ua}(p_n,jw)$ represents the acoustic transfer function that results from sound propagation from a speaker #n to the tympanic membrane when various acoustic factors are considered, including atmospheric propagation losses, effects of head, torso, neck, pinna, concha, ear canal, tympanic membrane, and middle ear impedance.

Transfer function measurements with a probe tube placed on the face-plate of the ICP may also be made. These measurements are referred to herein as $H_{fp}(p_n,jw)$, which represent the transfer function from a speaker #n to a face-plate (fp) of the ICP (discussed in more detail below), at a location representative of the microphone position on a face-plate of a simulated hearing aid.

Figure 8:
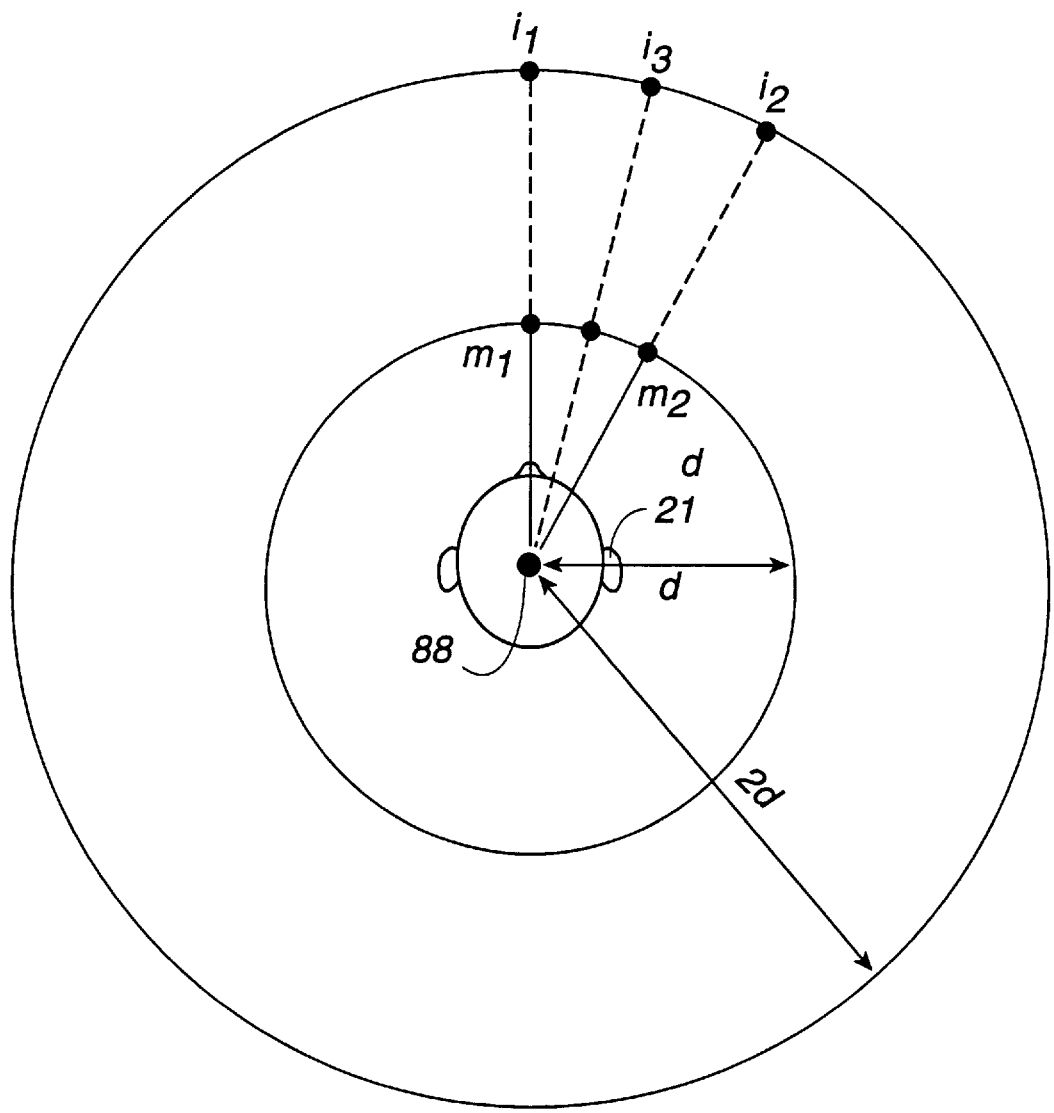
FIG. 8 is a schematic diagram showing an example of transfer function interpolation at a point $i_3$ from transfer functions, measured at points $m_1$ and $m_2$ in a two-dimensional transverse plane according to the invention.

Generally a transfer function $H(p_{(d,\theta,\alpha)}, jw)$ at an arbitrary point $p_{d,\theta,\alpha}$ in space at coordinates d, θ, and, α can be interpolated from the set of measured transfer functions as shown in FIG. 8. For example, it is known that the sound pressure from an audio source is inversely proportional to distance in normal atmospheric conditions. Furthermore, a transfer function of a point in space can be approximated by the weighted average of the two nearest measured transfer functions. FIG. 8. shows an example of an approximate transfer function $H(i_3,jw)$ interpolated in the transverse plane at point $i_3$ from transfer functions $H(i_1,jw)$ and $H(i_2,jw)$, which are also interpolated from transfer functions $H(m_1,jw)$ and $H(m_2,jw)$ measured with speakers #1 (89) and #2 (90).

Thus;

$$H(i_3,jw)=[H(m_1,jw)+H(m_2,jw)]/[2*L_{ai}(jw)] \quad [1]$$

where $L_{ai}(jw)$ is the atmospheric loss transfer function due to atmospheric absorption and spreading roll-off of sound.

Similarly, interpolation can be used to approximate any transfer function at an arbitrary point in a three-dimensional space from the weighted average of the nearest set of measured transfer functions. The accuracy of interpolated functions can be improved if additional measurements are made with additional speakers and/or speaker-head orientations. The preferred embodiment of the invention employs a practical compromise between the number of speakers, e.g. six in the embodiment of the invention described herein, and individual orientations, e.g. two: a front and a back orientation. Furthermore, non-linear weighting for transfer function interpolation may be more appropriate if determined from statistical data obtained from transfer function measurements of large number of individuals.

Other transfer functions measured by the VEA system include:

(1) the $H_{icp-rec}(jw)$ transfer function, which represents the ICP receiver to in-the-ear-canal electroacoustic transfer function, as measured by a probe when the ICP is positioned in the ear canal of the individual;

(2) the $H_{icp-mic}(jw)$ transfer function, representing the electroacoustic transfer function from an ICP speaker to the microphone of the hearing aid used during the hearing aid evaluation; and (3) the $H_{icp-fb}(jw)$ transfer function, representing the acoustic leakage, i.e. acoustic feedback, from the receiver of the ICP measured at face-plate of the ICP.

The transfer functions $H_{ua}(p_n,jw)$, $H_{fp}(p_n,jw)$, $H_{icp-rec}(jw)$, $H_{icp-mic}(jw)$, and $H_{icp-fb}(jw)$ are employed in various combinations to digitally synthesize acoustic signals, representing unaided, simulated aided, or aided listening conditions, with realism that is not possible with conventional evaluation and fitting methods.

Figure 9:
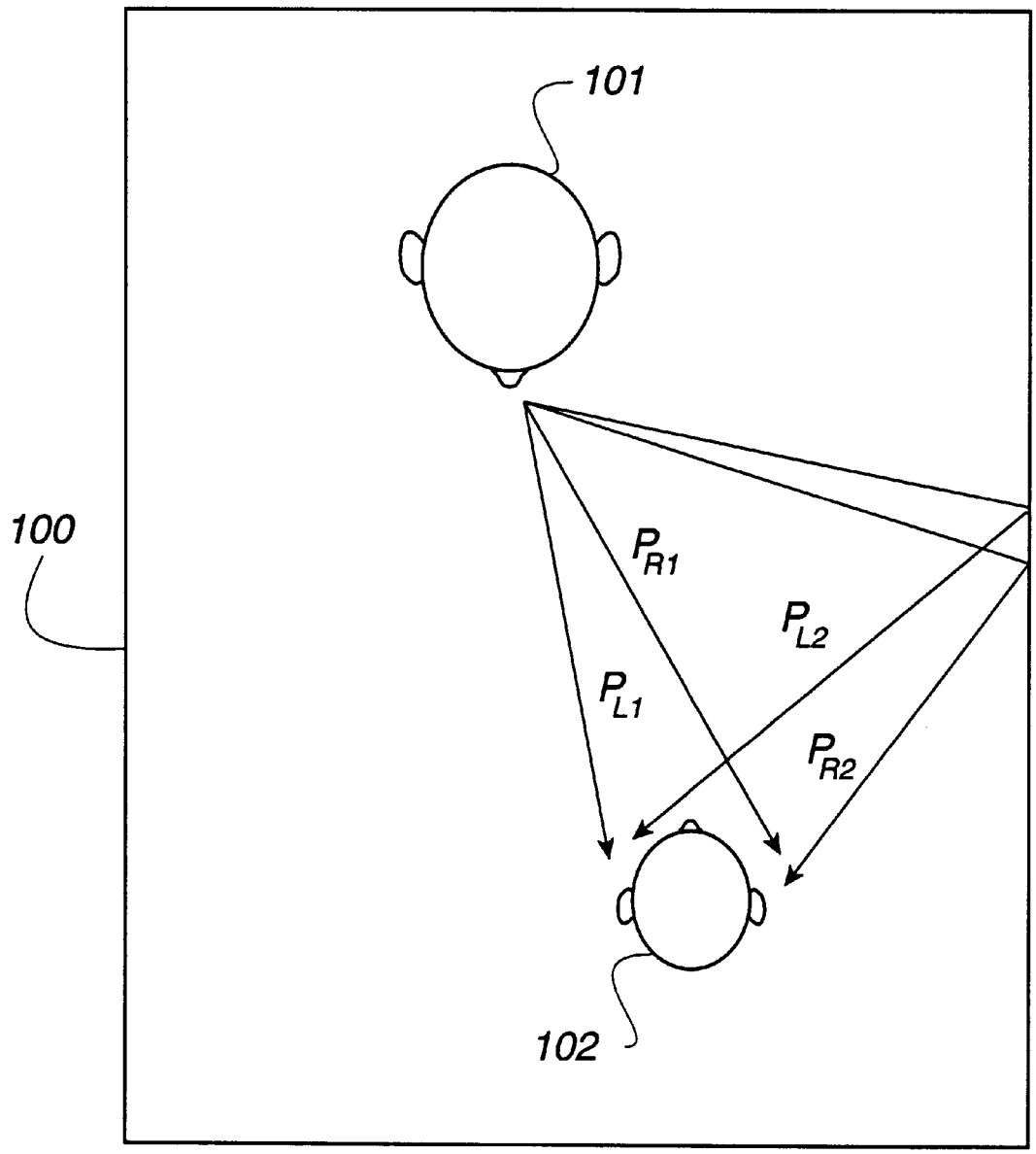
FIG. 9 is a schematic diagram showing an example of realization of a realistic listening scenario for unaided hearing evaluation conditions, and in particular showing a teacher-talker/child-listener scenario including direct acoustic paths $P_{R1}$ and $P_{L1}$ and early reflection paths $P_{R2}$ and $P_{L2}$ to the right and left ears of the child-listener according to the invention.

In FIG. 9, for example, a teacher-talker 101 and a child-listener 102 acoustic environment 100 is created as follows: direct acoustic paths $p_{R1}$ and $p_{L1}$, and reflection paths $p_{R2}$ and $p_{L2}$, for right and left ears of the child-listener 102 are represented by transfer functions interpolated from previously measured transfer functions of the child.

Figure 10:
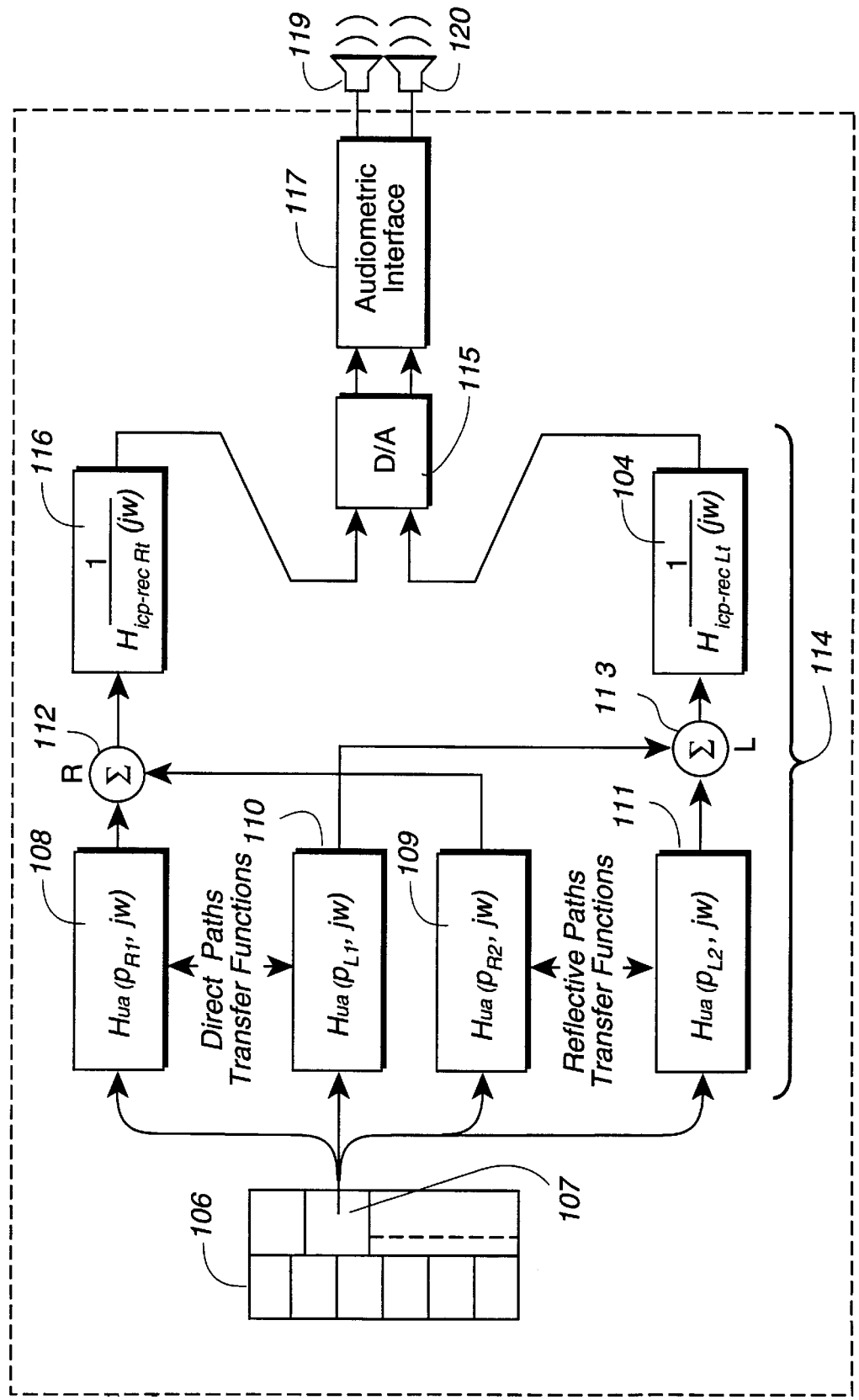
FIG. 10 is a block level schematic diagram showing an example of realization of a realistic listening scenario for unaided hearing evaluation conditions, and in particular showing a process representation of a teacher-talker/child-listener scenario during unaided evaluation according to the invention.

The acoustic realization of the environment of FIG. 9 is shown in FIG. 10, in which a digital audio file 107 that represents teacher-talker speech is retrieved from a system memory 106 and digitally processed by digital signal processor 114. The digital signal processor performs signal processes $H_{ua}(p_{R1},jw)$ 108, $H_{ua}(p_{L1},jw)$ 110, $H_{ua}(p_{R2},jw)$ 109 and $H_{ua}(p_{L2},jw)$ 111, which represent the paths $p_{R1}$, $p_{L1}$, $p_{R2}$, and $p_{L2}$, respectively. Right and left ear path processes are summed at summing nodes 112 and 113 and are further processed with inverse transfer functions, $1/H_{icp-rec}$-Rt(jw) (116) and $1/H_{icp-rec}$-Lt(jw) (104), for right and left ICP receivers 119/120, respectively.

The inverse transfer functions are provided to cancel the acoustic transfer function that occurs between the ICP receiver and the residual volume of the ear canal as the sound is delivered. The processed right and left digital signals are then converted to analog signals via a digital-to-analog converter 115 and routed to right and left ICPs via an audiometric interface circuit 117. The process of projecting a virtual audio image to a listener at a particular point in a three-dimensional space, such as teacher-talker speech to a child-listener, is referred to as spatialization.

Alternatively, live-voice signals from the operating clinician via the operating clinician microphone can be used, instead of digital audio data, for spatialization and delivery to the listener wearing the ICP pair. The virtual position and volume of the spatialized audio source are under the control of the virtual audiometer system of the present invention, as is explained in more detail below.

Transfer function measurements of linear time-invariant systems, such as the transfer functions $H_{ua}(p_n,jw)$, $H_{fp}(p_n,jw)$, $H_{icp-rec}(jw)$, $H_{icp-mic}(jw)$, and $H_{icp-fb}(jw)$, typically employs discrete or swept pure tone acoustic stimulus. Other stimuli include speech-noise, white-noise, and other speech-like noise signals. Pseudo-random noise sequences and other signals have also been used to reduce the time required to compute the transfer function. Computational methods include Fast Fourier Transform (FFT), Maximum-Length Sequence (MSL), and Time-Delay Spectrometry (TDS) (see Rife. D., Vanderkooy, J., *Transfer-Function Measurement with Maximum-Length Sequences*, J. Audio Engineering Soc., Vol. 37, No. 6, June 1989, pp. 418–442). The advantages of MSL and TDS measurement include reduction of room reflection effects on the transfer function. One important component of measured transfer functions used in the present invention is the direct path transfer function.

In the preferred embodiment of the invention, the VEA's probe microphones are calibrated at the head reference point when the VEA is first installed in its clinical setup. These calibration data, stored in the system memory, are subsequently used during transfer function measurements to correct for the unique frequency response characteristics of each probe microphone used and the unique characteristics of room acoustics.

Figure 11:
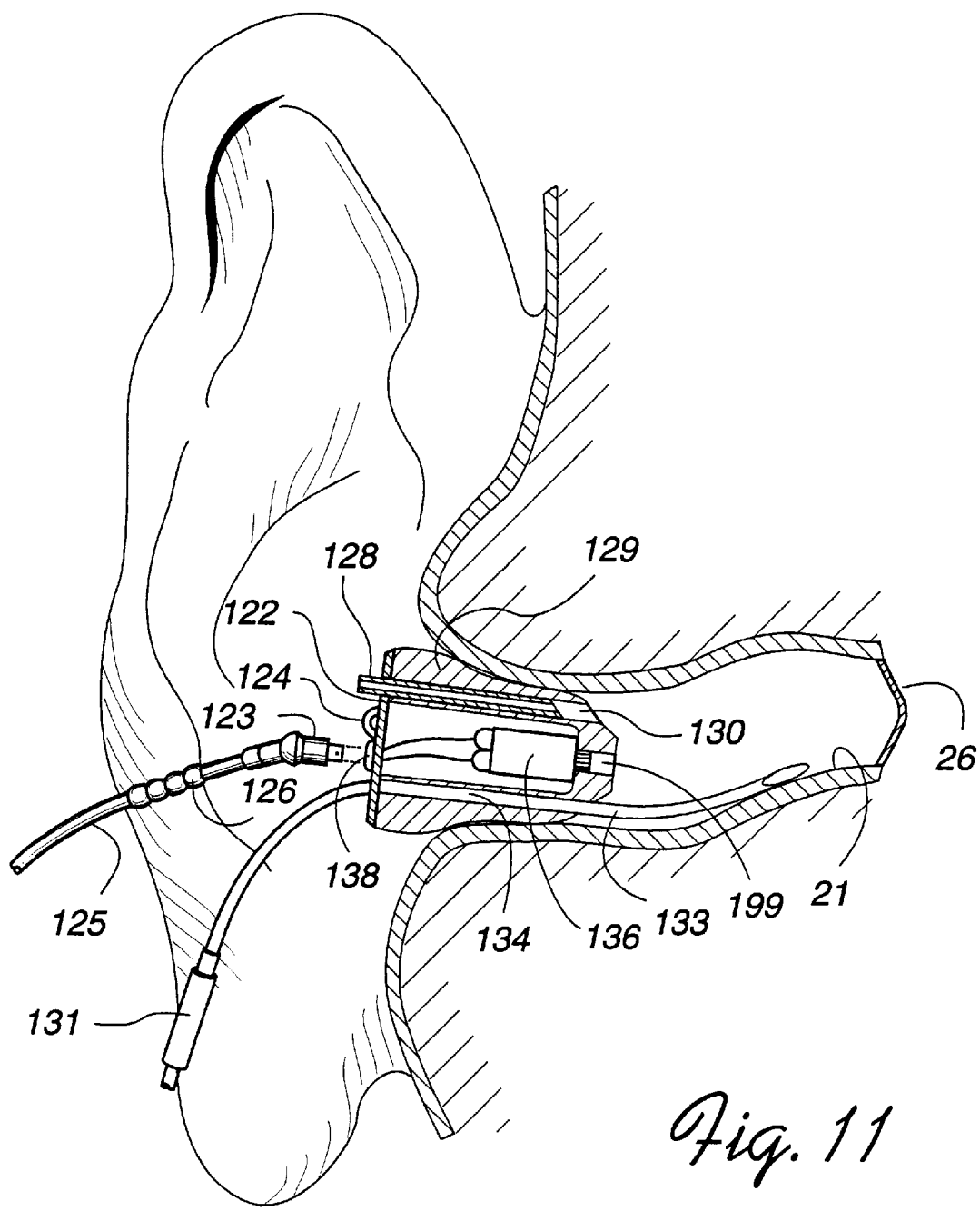
FIG. 11 is a partially sectioned, perspective view showing an intra-canal prosthesis (ICP) for an ICP-ITE representing hearing aids for shallow ear canal placement according to the invention.
Figure 12:
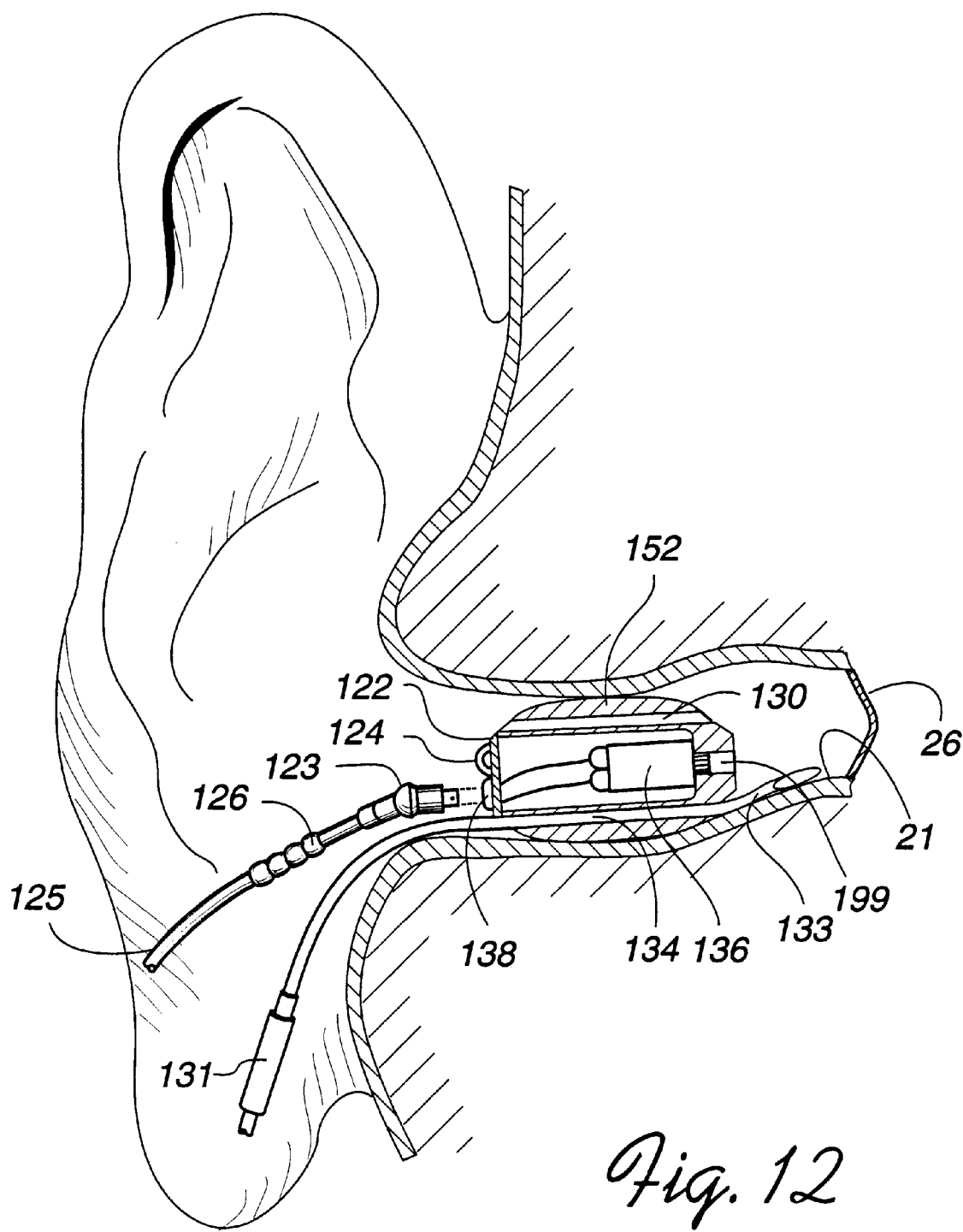
FIG. 12 is a partially sectioned, perspective view showing an intra-canal prosthesis (ICP) for an ICP-ITC representing hearing aids for deep ear canal placement according to the invention.
Figure 13:
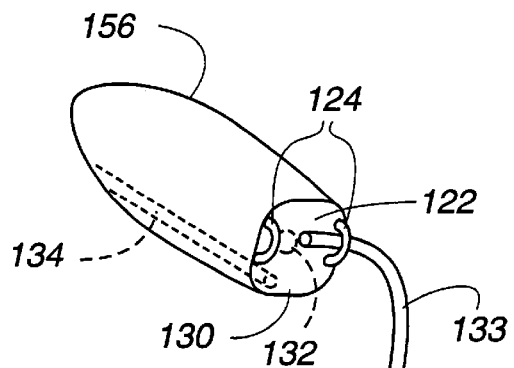
FIG. 13 is a perspective view showing an intra-canal prosthesis (ICP) face-plate end, including face-plate probe tube holders and probe tube placement according to the invention.
Figure 14:
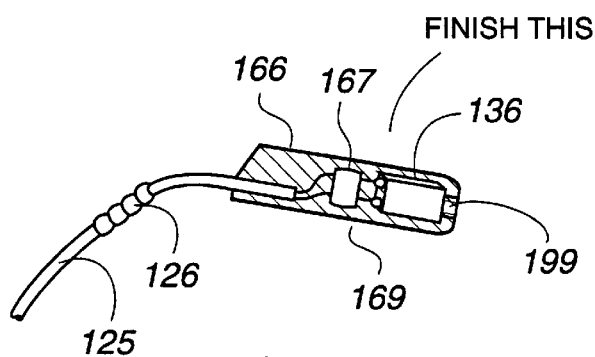
FIG. 14 is a partially sectioned, side view showing an ICP core module for a two-part ICP configuration according to the invention.
Figure 15:
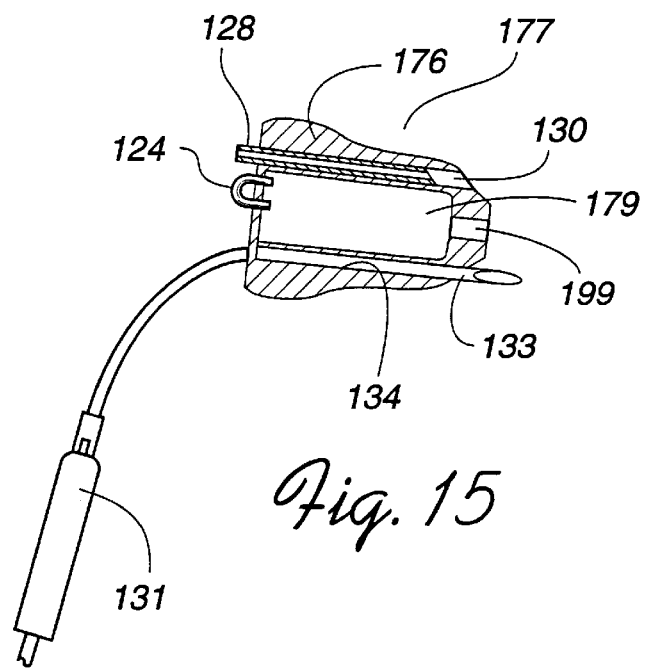
FIG. 15 is a partially sectioned, side view showing adjustable vent inserts and an ICP-ITE sleeve for an ICP-ITE configuration according to the invention.
Figure 16:
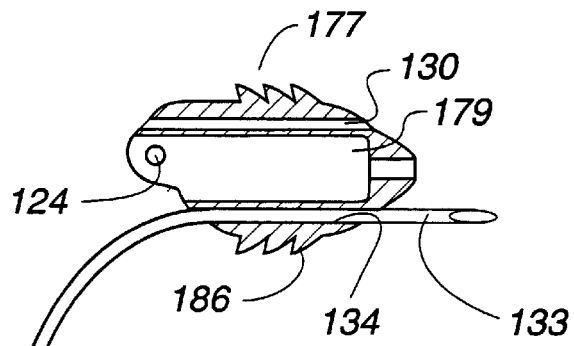
FIG. 16 is a partially sectioned, side view showing an ICP-ITC sleeve for a two-part ICP configuration according to the invention.
Figure 17:
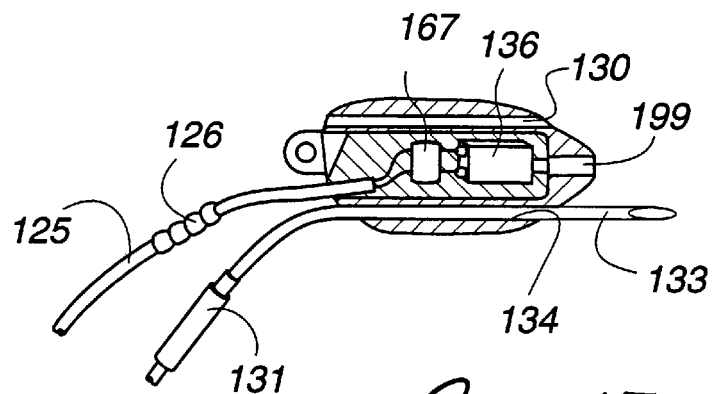
FIG. 17 is a partially sectioned, side view showing a complete two-part ICP-ITC assembly according to the invention.
Figure 18:
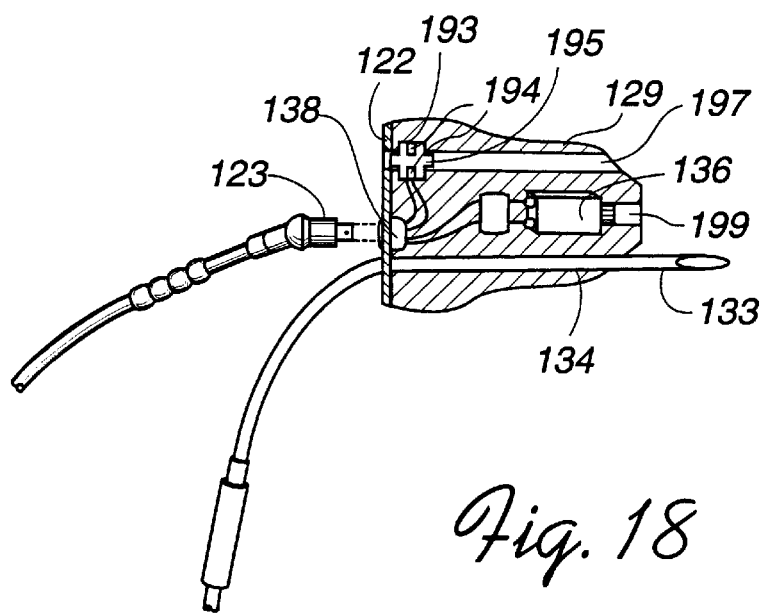
FIG. 18 is a partially sectioned, side view showing an ICP having a programmable vent according to the invention.
Figure 19:
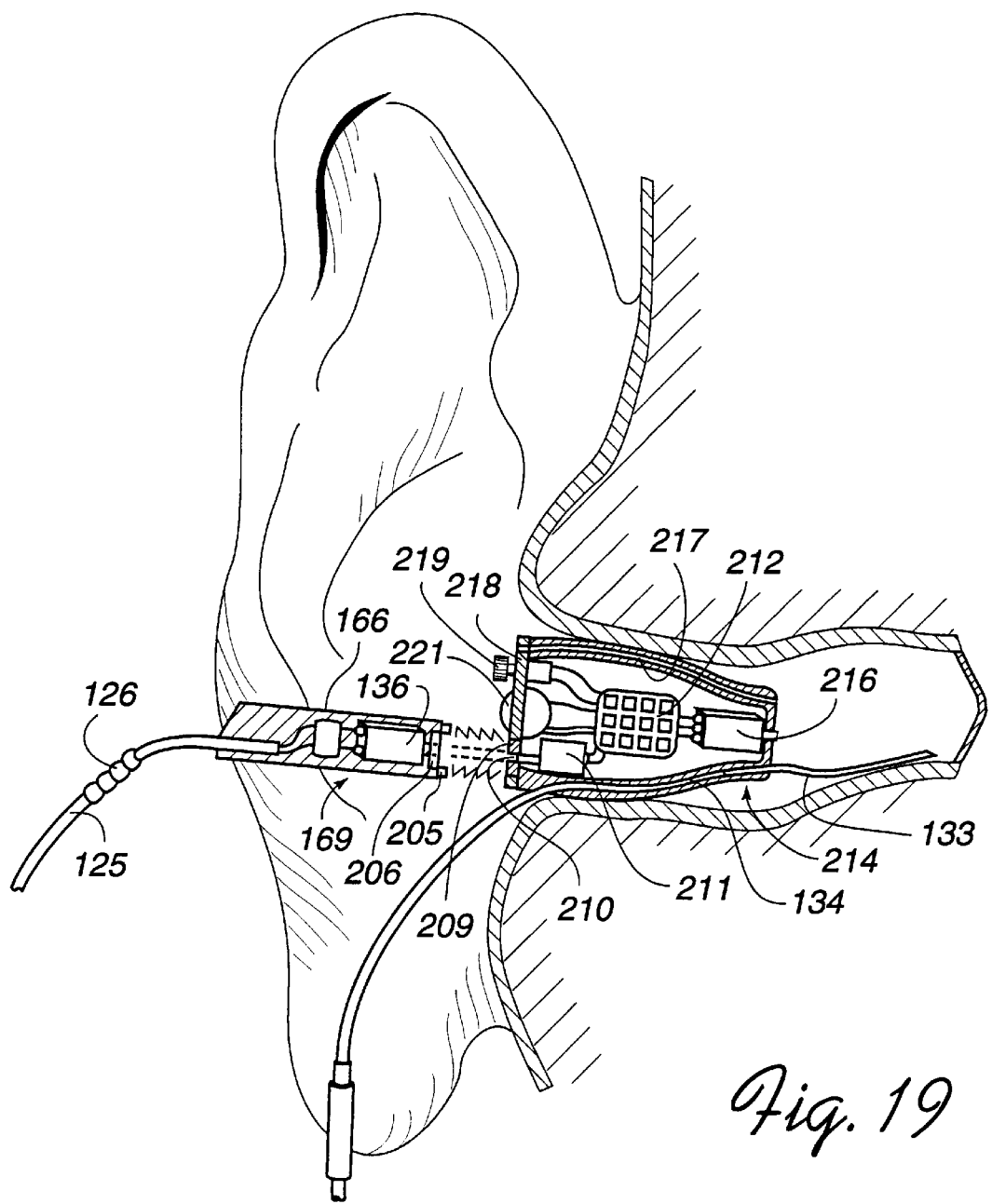
FIG. 19 is a partially sectioned, side view showing a hearing aid and direct acoustic coupling method to an ICP, including direct acoustic coupling via a magnetic attraction method according to the invention.
Figure 20:
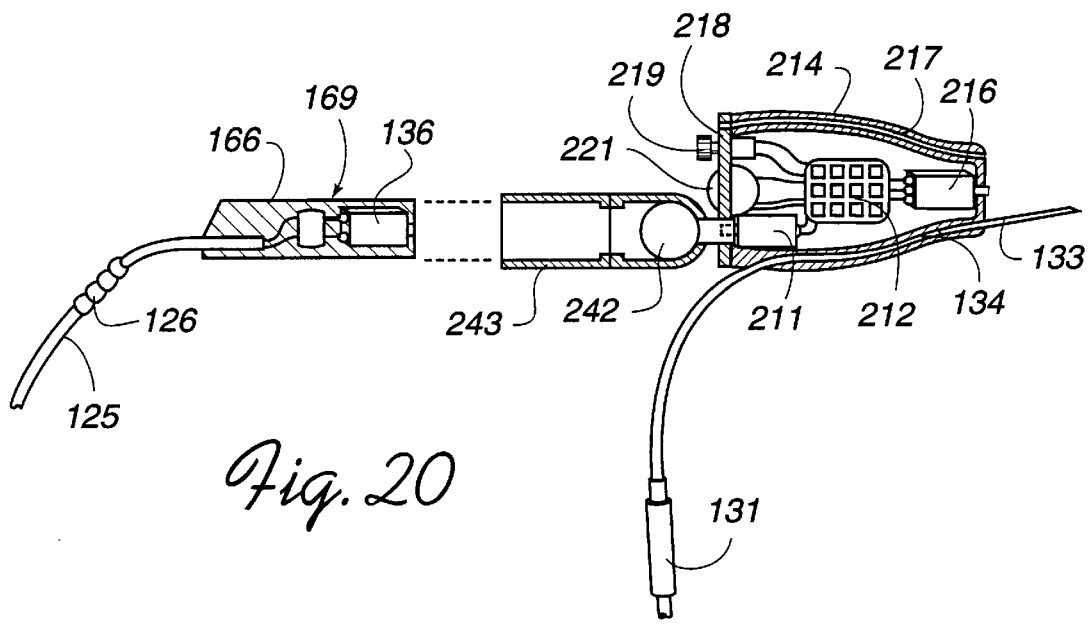
FIG. 20 is a partially sectioned, side view showing a hearing aid and direct acoustic coupling method to an ICP, including direct acoustic coupling via an acoustic coupler method according to the invention.
Figure 21:
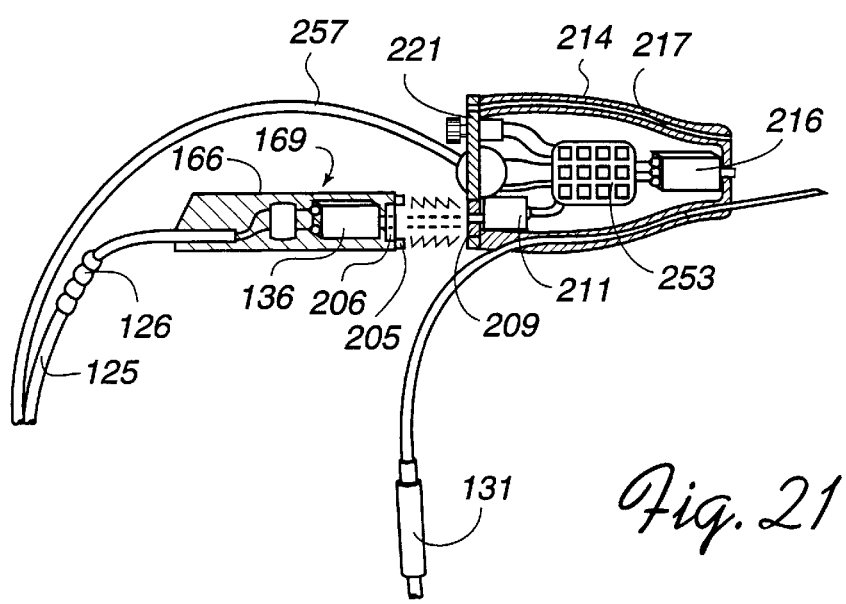
FIG. 21 is a partially sectioned, side view showing a hearing aid and direct acoustic coupling method to an ICP, including a programming and acoustic coupling interface according to the invention.
Figure 22:
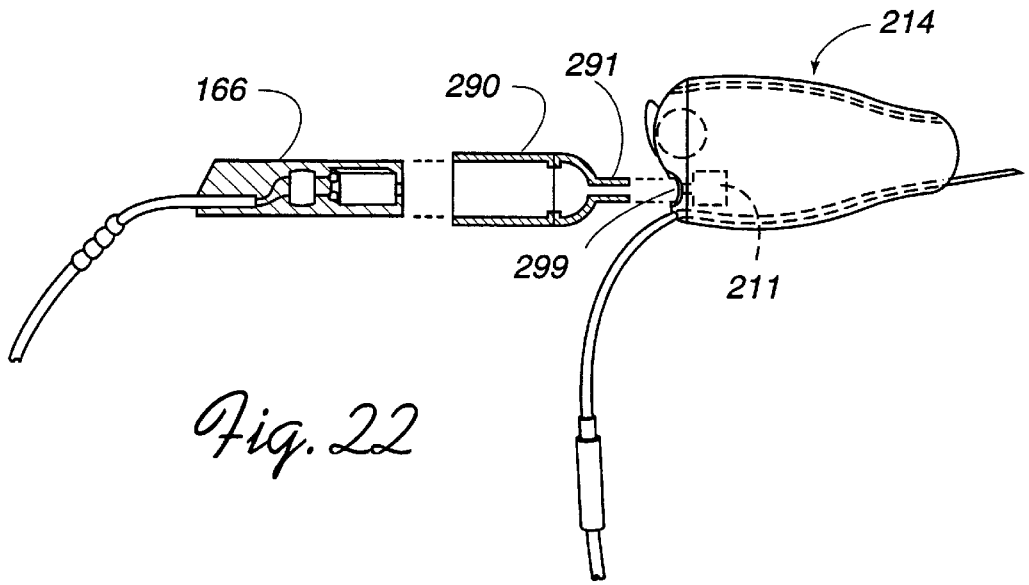
FIG. 22 is a partially sectioned, side view showing a hearing aid and acoustic coupling to an ICP via an acoustic coupler tip according to the invention.

FIG. 11 is a partially sectioned, perspective view showing an intra-canal prosthesis (ICP) for an ICP-ITE representing hearing aids for shallow ear canal placement; FIG. 12 is a partially sectioned, perspective view showing an ICP for an ICP-ITC representing hearing aids for deep ear canal placement; FIG. 13 is a perspective view showing an ICP face-plate end, including face-plate probe tube holders and probe tube placement; FIG. 14 is a partially sectioned, side view showing an ICP core module for a two-part ICP configuration; FIG. 15 is a partially sectioned, side view showing adjustable vent inserts for an ICP-ITE; FIG. 16 is a partially sectioned, side view showing an ICP-ITC sleeve for a two-part ICP configuration; FIG. 17 is a partially sectioned, side view showing a complete two-part ICP-ITC assembly; FIG. 18 is a partially sectioned, side view showing an ICP having a programmable vent; FIG. 19 is a partially sectioned, side view showing a hearing aid and direct acoustic coupling method to an ICP, including direct acoustic coupling via a magnetic attraction method; FIG. 20 is a partially sectioned, side view showing a hearing aid and direct acoustic coupling method to an ICP, including direct acoustic coupling via an acoustic coupler method; FIG. 21 is a partially sectioned, side view showing a hearing aid and direct acoustic coupling method to an ICP, including a programming and acoustic coupling interface; and FIG. 22 is a partially sectioned, side view showing a hearing aid and acoustic coupling to an ICP via an acoustic coupler tip, all according to the invention.

In the foregoing figures, those elements of the invention that are common to the various embodiments have a common numeric designator. For example, the ICP of FIGS. 11 and 12 each have a receiver 136, while the housing 129 in the embodiment of FIG. 11 is different from the housing 152 of the embodiment of FIG. 12.

The intra-canal-prosthesis (ICP), shown in FIGS. 11–22, consists mainly of a receiver 136, a receiver port 199, a probe tube 133 inserted in probe tube canal 134, vent inserts 128 inserted in vent canal 130, a probe microphone 131, a face plate 122, and a housing made of a flexible material, such as an acrylic. The ICP is generally designed to represent physical and electroacoustic characteristics of a desired type of hearing aid with the exception of the signal processing and generation, which is performed by the audio synthesizer board of the computerized virtual electroacoustic audiometer system. FIGS. 11 and 12 show ITE and ITC ICPs that represent hearing aids having shallow and deep canal placement, respectively.

The receiver 136 used in the preferred embodiment of the present invention (manufactured by the Knowles Corp. of Itasca, Ill.) was chosen for its acoustic characteristics, which are similar to receivers used in commercially available hearing aids, as well as its very low noise output characteristics. ICP receiver variations from simulated hearing aid receivers are stored in the VEA system memory as a correction transfer function used during various simulation processes. The probe tube 133, preferably made of a silicone rubber material and having a diameter of approximately 1 mm, is inserted in the probe tube canal 134 of the ICP as shown in FIGS. 11–22.

A vent canal 130 is preferably provided for pressure equalization in the ICP-ITC versions that have deep canal insertion depths (FIGS. 12 and 17), and to accommodate vent inserts for the ICP-ITE version having shallow canal insertion depths (FIGS. 11 and 15). In the ICP-ITE versions, a vent canal allows the insertion of various vent inserts into the vent canal to achieve desired in situ acoustic characteristics. For example, a vent insert of relatively large diameter may be used to reduce the occlusion effect that results from increased perceived volume of the individual's own voice. On the other hand, a smaller vent insert may be used to eliminate acoustic leakage from the receiver via the vent insert. A miniature connector socket 138 and connector plug 123 electrically connects the ICP to the VEA system via attached connector cable 125.

The VEA system, in conjunction with the probe microphone system, permits measurements of the occlusion effects versus ICPs and vent types, as is explained later. The ICP also contains two probe tube holders 124 and a placement handle 126 for placement of the probe tube, as shown in FIGS. 11, 12, and 17. FIG. 13 shows a more detailed illustration of a face plate 122, including the face plate tube holders 124. In the figure, a ICP/ITC sleeve 156, and a hearing aid microphone position 132 are also shown. This configuration is used when measuring acoustic leakage feedback and face-plate transfer functions.

The ICP housing (129, FIG. 11; 152, FIG. 12) is preferably made of a soft flexible material with acoustic baffling effects to provide comfort and acoustic sealing. Several versions of the ICP can accommodate a variety of ear canal sizes. For example, a small housing version is more suitable for pediatric populations, while a larger version is suitable for adults who have large ear canals. The ICP, shown in FIGS. 11 and 12 is preferably disposable to avoid contamination from individuals who have infected ear canals.

An alternate embodiment of the invention provides a two-part ICP configuration, as shown in FIGS. 14–17. A core part 169 (FIG. 14) is inserted in a variety of disposable sleeves 177, as shown in FIGS. 15 and 16. This option provides an economical alternative to the configuration shown in FIGS. 11–13 because only the sleeve component is disposable. The core part 169 is encapsulated in a protective material 166, preferably having semi-flexible properties. A decoupling capacitor 167 may be used to filter extraneous electromagnetic signals that cause audible noise.

The sleeve part shown in FIGS. 15 and 16 is typically made of flexible material, such as a soft acrylic, such that the ICP fits comfortably into a variety of ear shapes and sizes. FIG. 16 shows a sleeve suitable for deep canal insertions, representing ITC and CIC hearing aid types. Also shown in FIG. 16 is an acoustic baffle system 186 that provides an acoustic seal while the ICP is inserted in the ear canal.

FIG. 15 shows an ICP sleeve for shallow canal insertions representing ITE hearing aid types. The ICP core is inserted in the sleeve cavity 179 of any ICP, including those shown in FIGS. 15 and 16. The specific size of the ICP sleeve selected by the operating clinician depends upon the test performed, individual canal size, and hearing aid simulation requirements. An example of the combined parts of a core ICP and an ICP sleeve are shown in FIG. 17, which represents an ICP-ITC assembly.

FIG. 18 shows a variation of the vent mechanism where the size of the vent is electronically controlled and adjusted (see Zdeblick, K., *A Revolutionary Actuator For Microstructures*, Sensors Magazine, eb. 1993). This is accomplished by employing programmable micro-valve 193 (such as the NO-300 manufactured by Redwood Microsystems of Redwood City, Calif.) which contains a silicon diaphragm 194 which is to regulate the size of the vent attached to the vent canal 197 via the micro-valve port 195. Typical vent size range is between 0.032 and 1.5 mm, according to the voltage level supplied from the virtual electroacoustic audiometer module in response to operating clinician test selections.

The ICP is also used in a novel way to test a new type of hearing aids adapted to interface to the ICP, as shown in FIGS. 19–22. Unlike conventional hearing aid and aided hearing evaluation methods that typically employ remotely positioned speakers to deliver acoustic signals into the hearing aid microphone, the ICP of the present invention presents acoustic signals directly to the microphone 211 of the hearing aid 214. The acoustic coupling of the present invention spans a minimal distance typically less than 15 mm.

FIGS. 19 and 21 show an embodiment of the invention in which acoustic coupling is accomplished via a magnetic attraction method. In such method, the ICP receiver 136 is coupled to the hearing aid microphone 211 via magnetic attraction between a magnet disk 206 on the receiver end of the ICP and another magnet disk 209 near the hearing aid microphone port 210, and which is part of the face-plate 218 of a hearing aid 214, as shown in FIG. 19. A sealing ring 205 provides acoustic sealing to minimize leakage in the coupling. Also provided are a hearing aid battery holder 221, a hearing aid volume control 219, a hearing aid circuit 212, and a hearing aid vent canal 217, all representing conventional components of a hearing aid device.

Additionally, the embodiment of the invention shown in FIG. 21 provides a programmable hearing aid circuit 253 that allows dynamic ITE testing via control signals routed from the VEA over a programming cable 257. FIG. 21 shows an electrically programmable hearing aid with a programming cable 257 connecting the hearing aid circuit to the VEA of the present invention. These hearing aids contain circuits that are programmable or adjustable, typically via electrical signals. The shown programming interface at the face-plate is via the battery holder which is adapted to route programming electrical signals to the hearing aid circuit. The programming signals and interface methods are typically unique to the hearing aid model as provided by the specification of the hearing aid circuit used. These programming signals and interface methods are known to persons skilled in the art of hearing aid design. Other programmable hearing aids currently commercially available employ ultrasonic or infra-red signals with the appropriate signal interface circuits within the hearing aid.

An alternative acoustic coupling method couples the ICP receiver 136 to the hearing aid microphone 211 via a acoustic coupler 243, as shown in FIG. 20. The extended microphone port 242, unique to the present invention, also acts as a handle to facilitate insertion and removal of hearing aid 214 during its normal use.

Another embodiment of the invention, shown in FIG. 22, employs an acoustic coupler 290 adapted for insertion into a microphone port 299 of the hearing aid 214. The microphone port 299 is recessed to accommodate an acoustic coupler tip 291.

Another acoustic coupling method (not shown) employees a suction-cup ring to couple the ICP receiver to existing conventional hearing aids that are not equipped with special interface parts.

One major advantage of the direct acoustic coupling of the present invention is to improve the signal-to-noise ratio at the microphone of the hearing aid while the aid is being adjusted or evaluated. This is primarily accomplished by acoustically isolating the microphone of the hearing aid from ambient room noise via its coupling to the ICP.

Hearing aids of the present invention also employ a probe tube canal to allow for probe tube insertion and subsequent in-the-ear-canal acoustic measurements via the probe measurement system as shown in FIGS. 19–22. The conventional method of in-the-ear-canal measurements with hearing aids involve probe placements beneath the hearing aid which subjects the probe to pinching effects, thus affecting the accuracy of the measurement. Furthermore, placing the probe tube beneath the hearing aid creates an acoustic leakage path which causes oscillatory feedback. The probe tube canal of the present invention also provides an improved method of advancing the probe while the hearing aid is placed in the ear canal.

Figure 23:
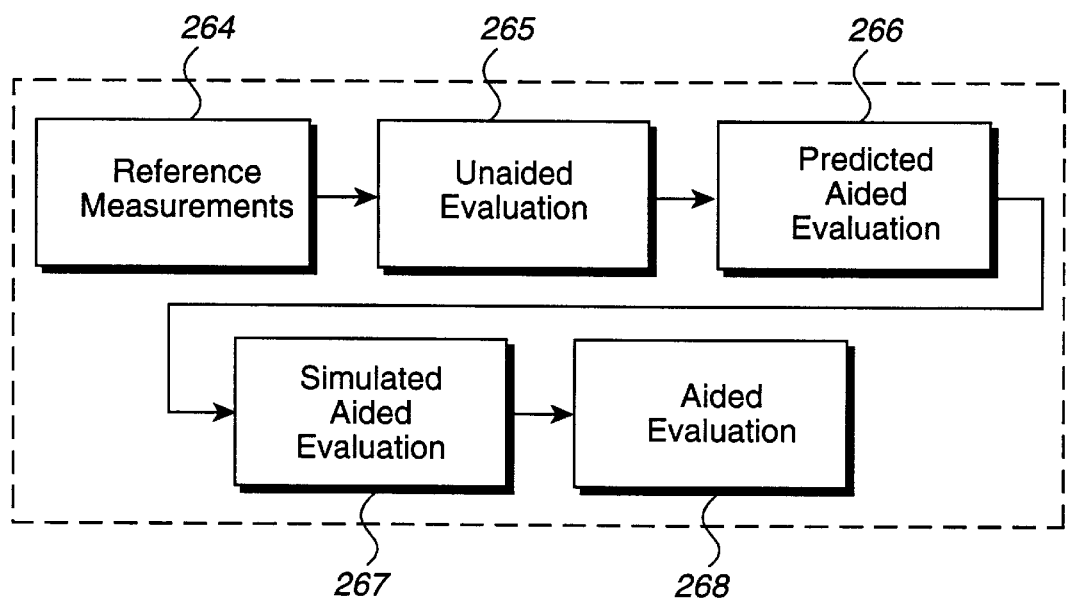
FIG. 23 is a block level schematic diagram showing an example of a fitting process provided by the virtual electroacoustic audiometer system according to the invention.

The sequence of these phases as outlined in FIG. 23 represents a typical fitting process unique to the system of the present invention. The fitting process offered by the virtual electroacoustic audiometer system in the preferred embodiment of the present invention is implemented in five phases: (1) reference measurements 264, (2) unaided hearing evaluation 265, (3) predicted aided evaluation 266, (4) simulated aided evaluation 267, and (5) aided evaluation 268. However, individual phases or a components of each phase can be administered individually, or in other sequence as suitable for the individual under hearing evaluation. Each process phase is implemented in a graphical module, as shown in FIGS. 24–28.

Figure 24:
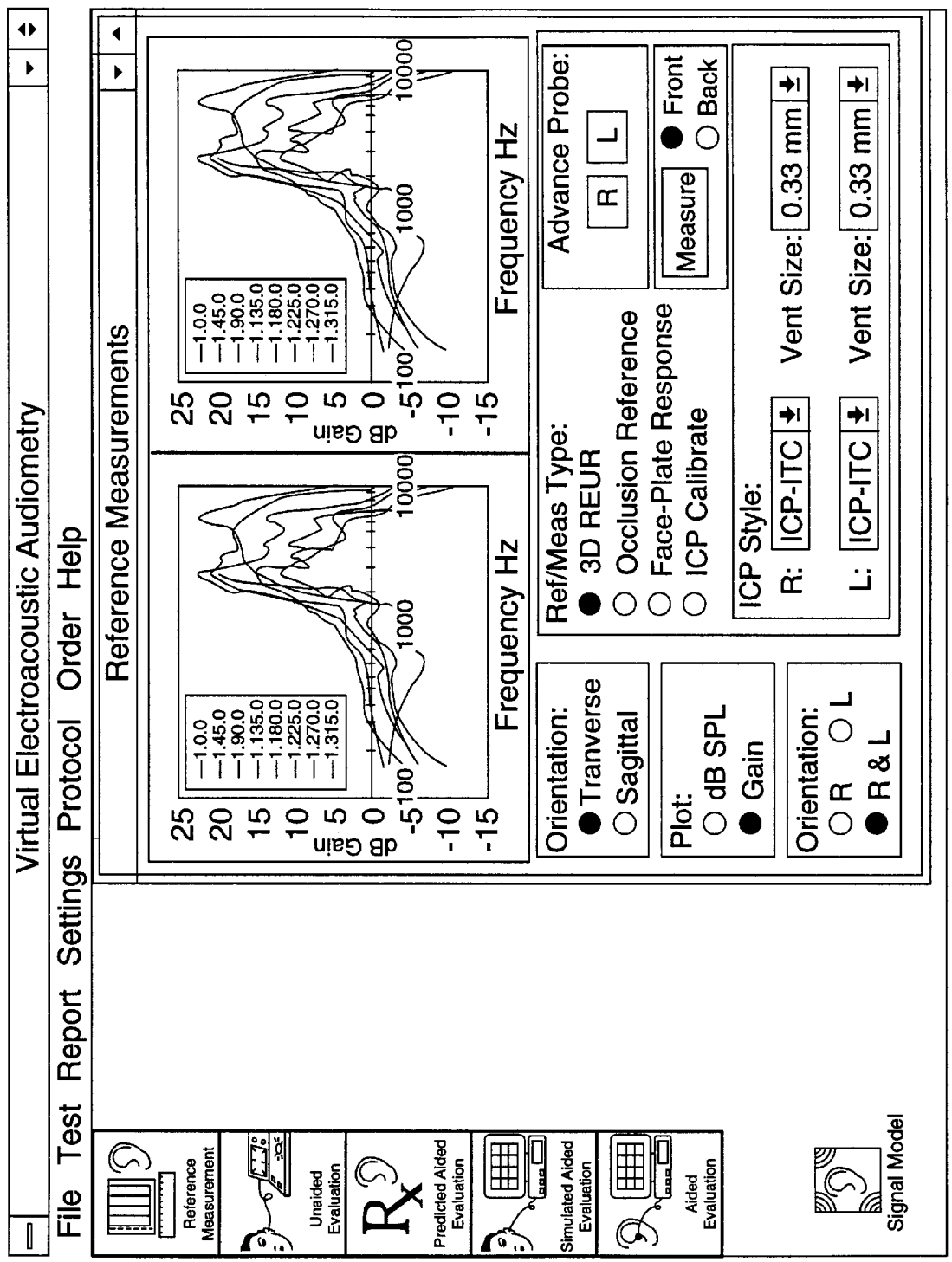
FIG. 24 is a graphic computer generated display showing a reference measurements module according to the invention.

The first phase, i.e. reference measurements, is implemented by a reference measurements module (FIG. 24) that contains a reference measurement window (shown open in FIG. 24) and a signal model window (shown iconized in FIG. 24). The reference measurement window allows for measurements of various transfer functions that are used later throughout the fitting process.

The unaided transfer function $H_{ua}(p_n,jw)$ described above, is measured when the 3D-REUR (3 Dimensional Real-Ear Unaided Response) option is selected. Measurements are obtained from the frontal (facing speaker #1) or back (facing opposite speaker #1) orientations, depending on the Front/Back option selected. Plots of right and left ear transfer functions can be displayed in either transverse or sagittal plane depending on the Transverse/Sagittal option selection. FIG. 24 shows a set of 8-paired $H_{ua}(p_n,jw)$ transfer functions in the transverse plane. The measurement is performed by positioning the individual centrally to the speaker array (discussed above) and placing right and left probe tubes in their respective unoccluded ear canal.

Another novel feature of the invention is the ability to measure and quantify the occlusion effect of the simulated hearing aid, as well as the fitted hearing aid. However, before the occluded measurement is taken, a reference measurement with the ear canal unoccluded must be taken. The procedure, briefly described here, is to request the individual to utter a vowel, preferably a vowel with high energy contents in its low frequency spectrum, such as "ee." A measurement is taken with the probe positioned near the tympanic membrane. The occlusion effect reference measurement, i.e. unoccluded, is saved for occlusion effect measurement with the ear canal occluded using either the ICP or the hearing aid, as is explained below. The occlusion effect reference measurement is performed when the occlusion reference option is selected.

The face-plate transfer function $H_{fp}(p_n,jw)$ (plots not shown) is measured when the Face-Plate Response option is selected. The ICP is placed in the ear and the probe tube tip is placed in the microphone position 132 of the face-plate as shown in FIG. 13.

The ICP-receiver to real ear transfer function, $H_{icp-rec}(jw)$ is measured when ICP Calibrate option is selected. This requires the probe tube to be inserted in the probe tube canal of the ICP, and the tip of the tube near the tympanic membrane.

Figure 30:
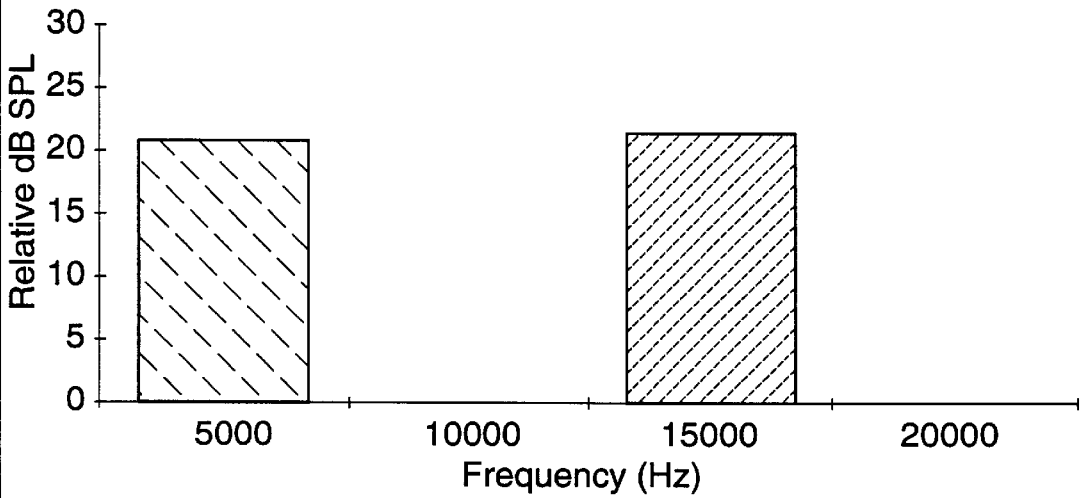
FIG. 30 is a bar graph plotting the measured SPL for 5 kHz and 15 kHz during probe advancing at 6 mm from tympanic membrane according to the invention.
Figure 31:
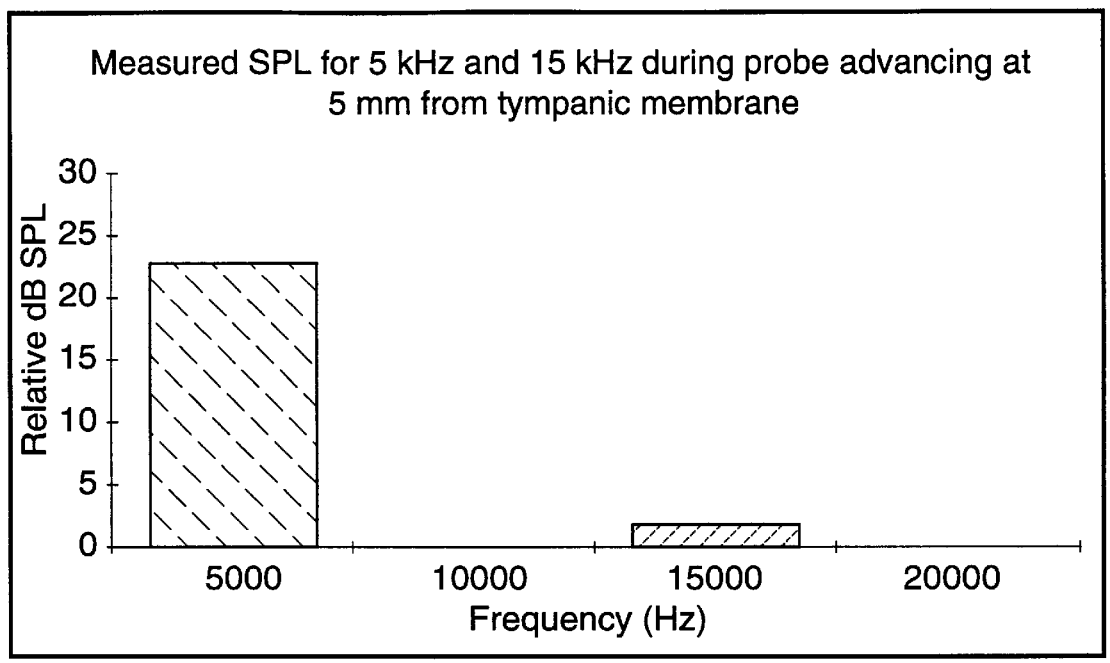
FIG. 31 is a bar graph plotting the measured SPL for 5 kHz and 15 kHz during probe advancing at 5 mm from tympanic membrane according to the invention.
Figure 32:
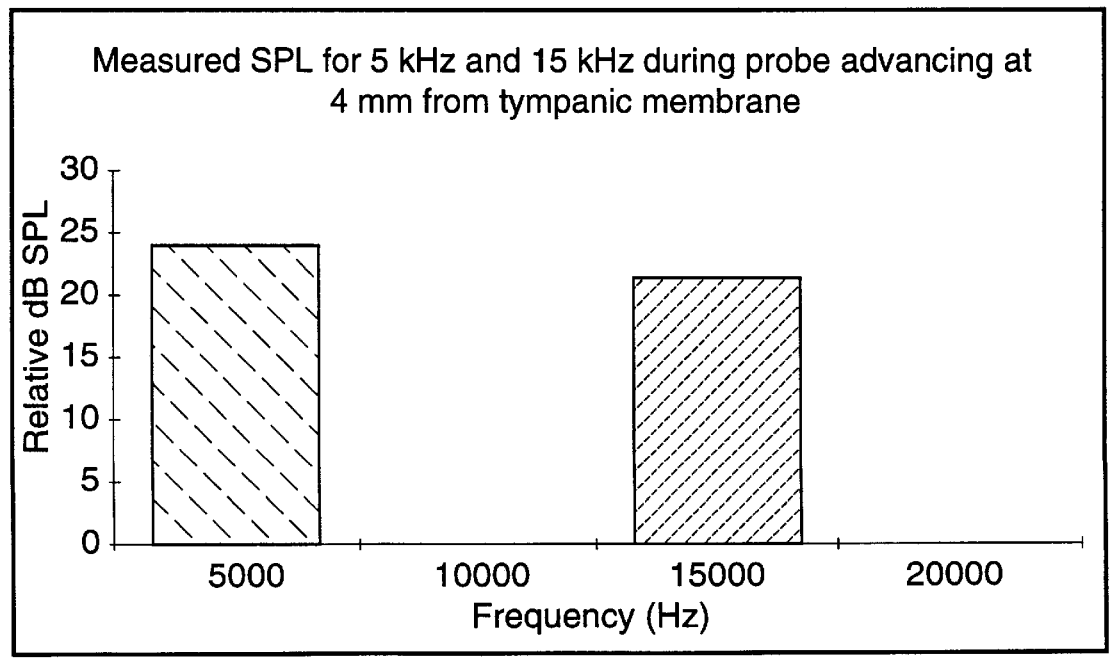
FIG. 32 is a bar graph plotting the measured SPL for 5 kHz and 15 kHz during probe advancing at 4 mm from tympanic membrane according to the invention.

To facilitate the proper placement of the probe in the ear canal during various response and calibration measurements, a novel method is employed to optimize such probe placement within the ear canal, and specifically to minimize the effects of standing waves present in the ear canal due to wave reflections from the tympanic membrane. The frequency dependent standing wave patterns are well characterized and known to persons skilled in the art of acoustics and particularly real ear acoustic measurements. The new method of the invention involves acoustic presentation of a dual tone, one at a low frequency in the range of 1 kHz to 5 kHz, and a second at a range of 15 kHz to 20 kHz. The acoustic response to tone signals delivered either via a speaker or the ICP receiver, depending on measurement, is continuously measured by microphone probe system and displayed on the monitor, as shown in FIGS. 30–32.

Figure 29:
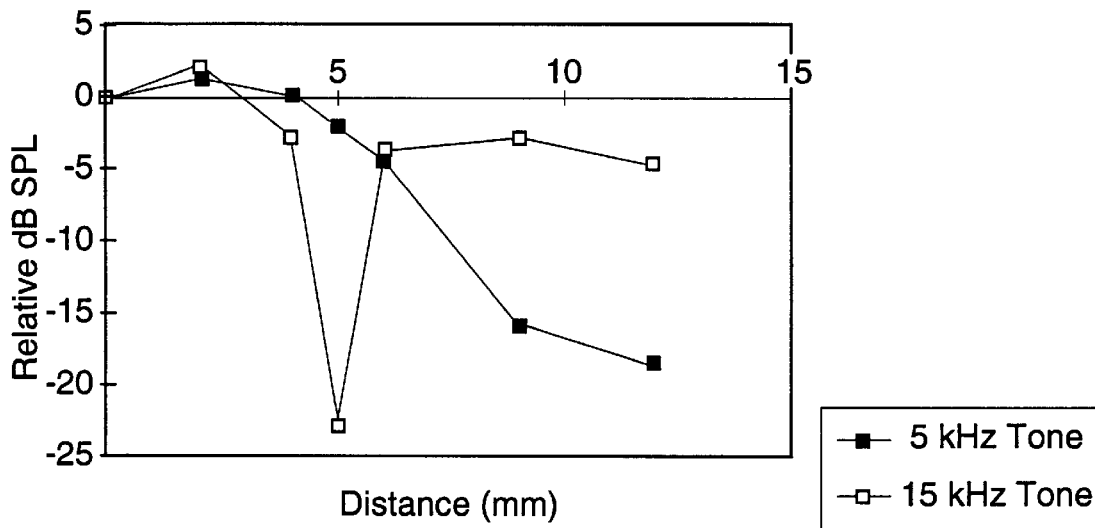
FIG. 29 is a line graph plotting the variability of measured SPL versus distance of probe tip from tympanic membrane for 5 kHz and 15 kHz tones for an individual according to the invention.

A plot of the acoustic response in an ear of an individual for each tone, shown in FIG. 29, indicates a characteristic rise in the low frequency response and a notch in the high frequency response as the probe is advanced closer to the tympanic membrane. This notch occurs at approximately 5 mm from the tympanic membrane for the 15 kHz tone. Monitoring of the relative response characteristics during probe insertion provides a visual and computer-assisted method to indicate proper probe positioning as shown in the spectrum plots of FIGS. 30–32. The end of this procedure is generally indicated when a significant notch, typically exceeding 15 dB as shown in FIG. 31, followed by a significant rise in the high frequency, i.e. second tone, response.

The low frequency, i.e. second tone, response shows only a small increase, within 3 dB, as the probe is inserted closer to the tympanic membrane. Although probe tip to tympanic membrane distance approximation is possible with this procedure, the object of this procedure is to position the probe such that minimal standing waves are present at frequencies of interest during transfer function measurements. For example, if unaided response measurements up to 6 kHz are desired, advancing the probe until detecting a notch in 15 kHz response ensures measurement errors not to exceed 2.5 dB at 6 kHz. Improved accuracy can be achieved by selecting a higher frequency for the second tone, although this increases the chance of advancing the probe too far, resulting in touching the surface of the tympanic membrane, an occurrence that is generally safe but that may cause discomfort.

Other combinations of tones, including a single, triple, composite, and other signals can also be used to implement the above procedure of continuously measuring the response to various acoustic stimuli and detecting an appropriate stopping point during probe advancement, with little regard to probe distance to the tympanic membrane. The appropriate probe position is referred to hereafter as the probe reference point.

Figure 25:
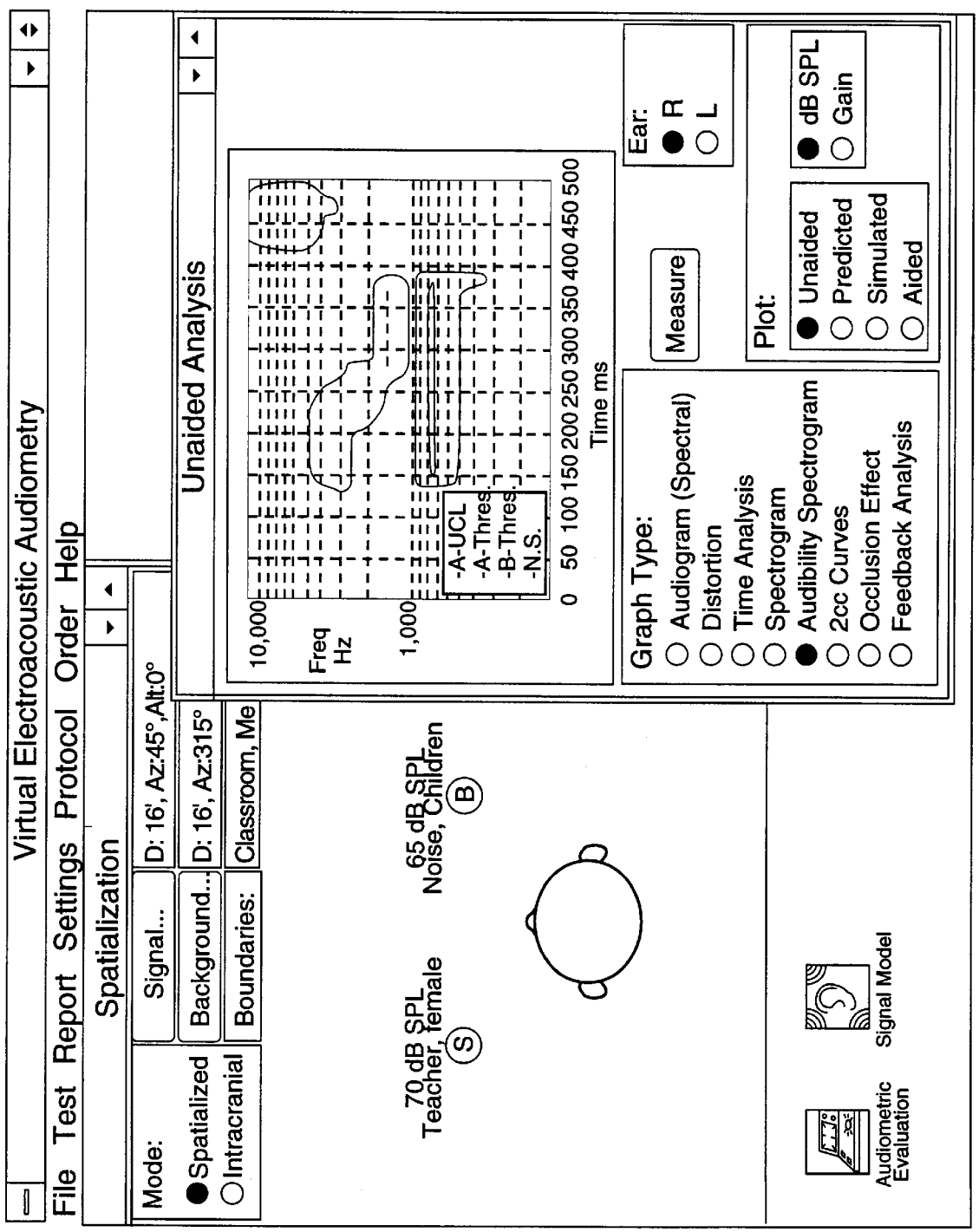
FIG. 25 is a graphic computer generated display showing an unaided evaluation module according to the invention.

The second phase, unaided evaluation, is implemented by an unaided evaluation module, shown in FIG. 25, which consists of an unaided analysis window, shown open in the figure; a spatialization window, also shown open; a signal model window, shown iconized; and an audiometric evaluation window, also shown iconized.

The unaided analysis window allows for various in-the-ear-canal measurements and displays for hearing evaluation in the unaided condition while the ICP is inserted in the ear canal. Measurements and plots include Audiogram spectrum, Distortion, Time Analysis, Spectrogram, and 2-CC curves. Acoustic stimuli, measurement methods, and associated plots for these tests are known to persons skilled in the arts of audiology and signal analysis. However, the Audibility Spectrogram is a new feature that is unique to the present invention as described below.

The Audibility Spectrogram is a spectral plot showing the audibility of a signal with respect to the hearing profile of the individual and the critical audibility features of an acoustic signal. The audibility spectrogram is essentially a three-dimensional matrix represented in a two-dimensional plot that indicates signal dynamics (time) and Critical Audibility Regions (CAR) versus frequency, as shown in FIG. 25. CARs, shown as the outer contours, are specific to each signal segment that is selected from the signal model window. CARs of a speech segment are defined by the critical sound features, such as the energy of significant formats in vowels, the energy of fundamental frequency of voicing, the energy of aperiodic frequency sounds, and other criteria known to effect intelligibility, detection, or identification, depending on the signal model selected.

The Audibility Spectrogram plots are derived by combining spectrograms of analyzed signals and defined CARs, and probe measured spectrograms computed and compared with the measured hearing profile of the individual at the CARs. Measured spectrogram values that fall below the threshold of hearing for the individual are assigned to Below Threshold (B-Thresh) values which define the outer contour region, within the CAR; while measured spectrogram values that exceed the threshold of hearing within CAR are assigned Above Threshold (A-Thresh) values which define a region within the Below Threshold region; and measured spectrograms values that exceed the uncomfortable loudness level (UCL) of the individual are assigned Above-UnComfortable Loudness level (A-UCL) values which define the inner-most contour regions.

The resulting color-coded plot is typically contour shaped for speech signals. However, any type of acoustic signal can be assigned CARs and a corresponding audibility spectrogram based on the individual's measured hearing profile. The objective of the Audibility Spectrogram plot is to provide a quick graphical means of indicating the audibility of dynamically received acoustic signals by taking in consideration the individual's hearing profile and the critical audibility features of a signal model. This plot is particularly important in hearing aid fitting optimization processes during predicted aided, simulated aided, and aided evaluation.

The spatialization window permits selection of signal presentation mode, either in Spatialized or Intracranial modes. Spatialized mode presents selected sources and background signals to be delivered to both ears via inserted ICPs according to the selected spatial relationship of head, sources, background, and boundaries, as shown in FIG. 25. Spatial relationships include the distance between the audio source and the head reference point (d), azimuth angle ($\theta$), and altitude angle ($\alpha$).

Various individual and calibration transfer functions are employed to synthesize audio signals with realistic listening effects. Signal sources and corresponding levels are selected from the Signal Model window (not shown). Intracranial mode, on the other hand, offers the conventional sound presentation method where selected signals and corresponding levels are delivered without spatialization to one or both ears.

The Signal Model window permits the selection of source and background signals and corresponding level. Source selection may be of pure tone type, speech, music, or any signal of audiological significance. Background signals are typically competing speech, environmental noise, and other signals of audiological significance. The level of signals selected in the spatialized mode is preferably in dB SPL calibrated to 1 meter from the source in free field. The measured in-the-ear-canal acoustic response is preferably displayed in dB SPL as measured by the probe microphone system.

In the intracranial mode, source and background signals are routed to right, left, or both ears as in conventional audiometry. The level of signals selected in the intracranial mode is preferably in dB SPL. The $H_{icp-rec}(jw)$ transfer function measurement via the ICP calibration procedure described above permits level selection in dB SPL. Furthermore, measurements via the probe microphone system can be made as needed to ensure that the probe and the ICP remain properly positioned in the ear canal.

A specific selection of source and background signal type, levels, and spatialization mode is defined as a signal model. One or more signal models can be selected, saved, and retrieved by the system for presentation and analysis purposes. A signal model can represent any individual or a combination of acoustic signals/scenarios, including speech, background noise, music, pure tone, masking noise, composite signals, and other audiologically significant signals.

The audiometric evaluation window, shown iconized, allows for various conventional audiometric measurements to be taken. This includes threshold audiogram, most comfortable level (MCL), uncomfortable loudness level (UCL), speech reception threshold (SRT), and various other audiometric measures known to persons skilled in the art of audiology. However, unlike conventional audiometry where transducers are calibrated in various acoustic couplers and measurements are measured in relative hearing level (HL) terms, the preferred method measures the in-the-ear-canal response in absolute sound pressure level (SPL) terms.

Another feature of the invention relates to the modes of audiometric signal presentation. As described above, spatialized or intracranial listening modes selected from the Spatialization window, not only affect the presentation selected from the Signal Model window, but also the Audiometric Evaluation window as well. For example, a standard audiological word list such as NU-6 or W-22, commonly used in conventional speech audiometry, can be presented in the conventional intracranial mode, or alternatively, in the spatialized mode unique to the invention.

The signal process of a spatialized unaided evaluation involves the unaided transfer function $H_{ua}(p_n,jw)$, interpolated based on selections of the spatialization window, and the $H_{icp-rec}(jw)$ transfer function. A signal process implementation of a particular spacialized unaided evaluation is shown in FIG. 10.

The third phase, the predicated aided evaluation, is implemented by the predicated aided evaluation module. This module, shown in FIG. 26, allows the operating clinician to select a hearing aid and predict its performance without the involvement of the hearing-impaired individual. The module consists of a Hearing Aid Select/Adjust window, shown open; a Predicated Analysis window, shown open); a Signal Model window, shown iconized; a Spatialization window, shown iconized;and the Audiometric Evaluation module. The Signal Model, Spatialization, and Audiometric Evaluation windows are essentially identical to those described in the Unaided Evaluation phase.

The Hearing Aid Select/Adjust window permits hearing aid selection and subsequent adjustment. The predicated results of the selection/adjustment are shown on the selected plots of the adjacent Predicted Analysis window. Hearing aid selection can be automatic or manual, depending on the hearing aid selection Automatic/Manual option selected. Automatic selection involves selecting one or more hearing aids based on the fitting algorithm selected, and various other criteria selected by the hearing-impaired and the operating clinician. Conventional fitting formulae and methods, such as POGO, Berger, and NAL-R, are provided.

The preferred fitting method is the dynamic audibility method which employs a rational such that Audibility Spectrogram is optimized. This corresponds to plots that maximize the Above-Threshold (A-Thresh) contour areas while minimizing Below-Threshold (B-Thresh) and Above-UnComfortable loudness Level (A-UCL) contour areas. Hearing aid models that best match the selected criteria are automatically retrieved from the system memory.

Alternatively, manual selection can be made by choosing one or more hearing aid models from the available list of models. A hearing aid model contains all of the necessary electroacoustic parameters that are used for signal processing of a signal model. The results of the signal process are used in the Predicted Analysis window for analysis and plotting purposes. Hearing aid parameters of a selected hearing aid model are adjusted automatically or manually depending on the hearing aid adjustment Automatic/Manual option and the fitting method selected.

A hearing aid control parameter set is typically unique to the hearing aid model selected. In the example window shown in FIG. 26 with hearing aid model DigiLink 100 selected, the control parameters are: volume control (VC), Low Frequency Cut (LFC), compression Threshold Knee (TK), Microphone type (MIC), Receiver type (REC), and Vent Size selection which reflects vent size of the ICP inserted. If a different vent size is selected, either manually via the vent insert selection, or electronically via the programmable micro-valve vent selection, a new $H_{icp-spkr}(jw)$ transfer function is preferably measured to improve the accuracy of the analysis.

Figure 33:
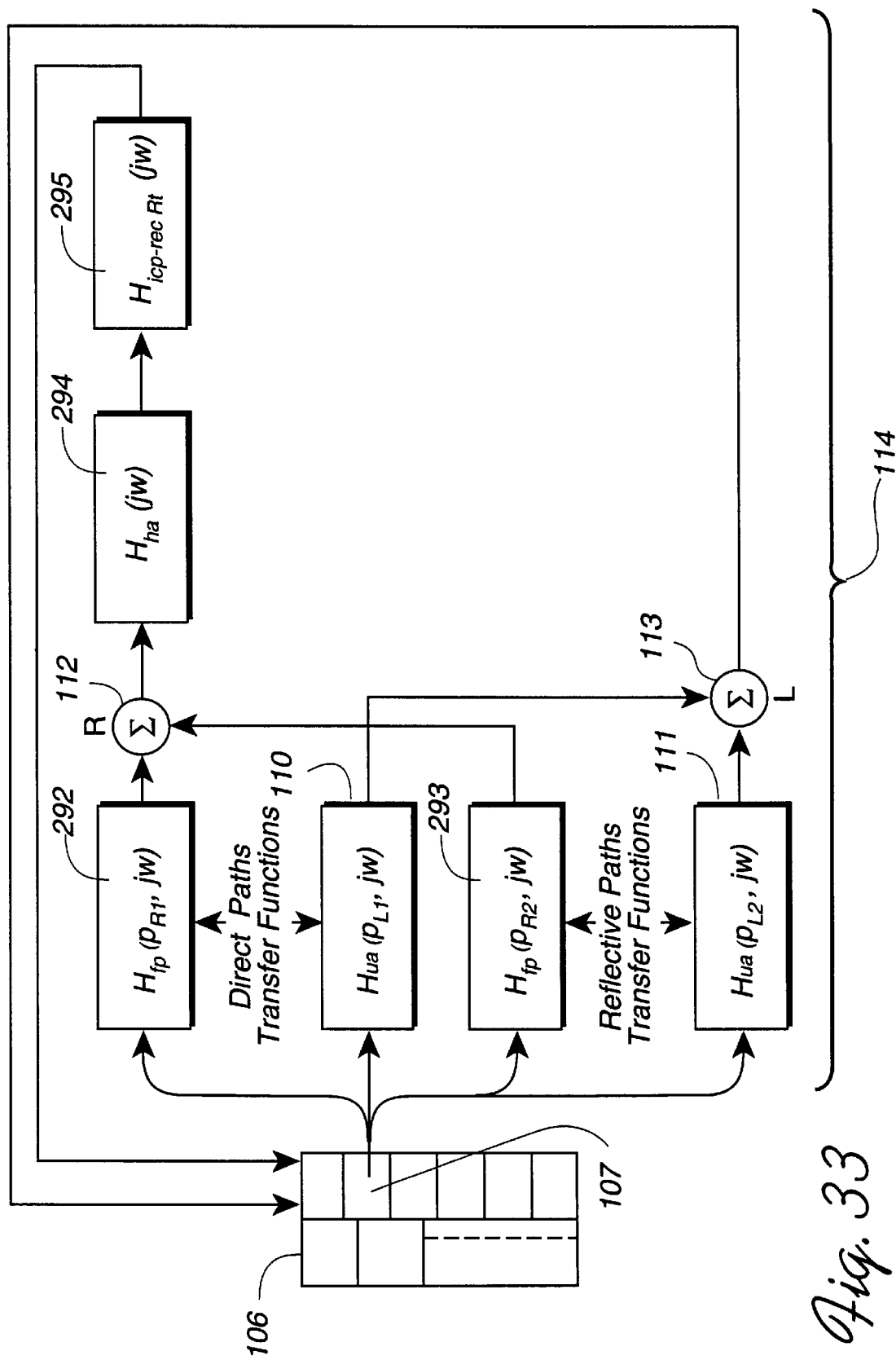
FIG. 33 is a block level schematic diagram showing an example of a teacher-talker/child-listener scenario using predicted aided evaluation for the right ear according to the invention.

The predicted analysis window is essentially identical to the unaided analysis window, described above, with the exception of the signal processing model that includes the measured face-plate transfer function $H_{fp}(p_n,jw)$ (292, 293; FIG. 33), hearing aid transfer function $H_{ha}(jw)$ (294; FIG. 33), and the measured ICP receiver to real-ear $H_{icp-rec}(jw)$ transfer function for the aided ear (295; FIG. 33). The hearing aid $H_{ha}(jw)$ transfer function is typically non-linear and varies depending on the hearing aid selected. The total hearing aid transfer function $H_{ha-t}(jw)$ typically includes transfer functions of the microphone $H_{mic}(jw)$, hearing aid circuit $H_{ha-rec}(jw)$, and the receiver $H_{ha-rec}(jw)$. The transfer function $H_{ha}(jw)$ differs from $H_{ha-t}(jw)$ by excluding the hearing aid receiver and, instead, including a receiver correction transfer function $H_{Rec-corr}(jw)$, that defines the difference between the predicted hearing aid receiver and the ICP receiver employed. This correction transfer function $H_{Rec-corr}(jw)$ is typically a linear transfer function and is supplied by the VEA system.

The predicted aided analysis process for an aided right ear and unaided left ear for a child-listener/teacher-talker scenario is shown in FIG. 33. The results of the digital signal process are stored in the system memory 106 for analysis and display.

Figure 26:
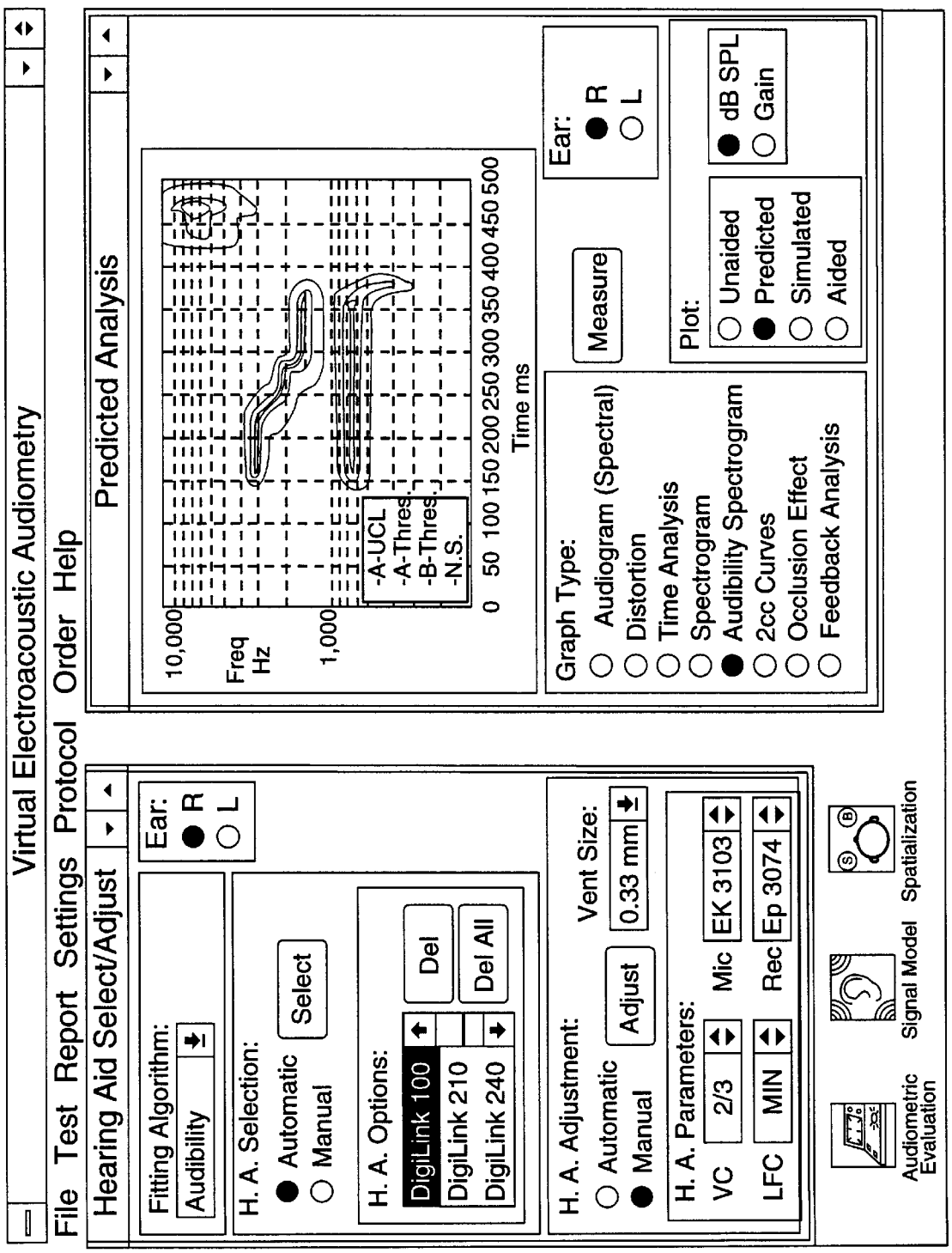
FIG. 26 is a graphic computer generated display showing a predicted aided module according to the invention.

The analysis of the predicted data in the system memory includes audibility analysis as described above. The plotting includes an Audibility Spectrogram that indicates audibility contours of Below-Threshold, Above-Threshold and Above-UCL with respect to critical audibility regions (CRAs). FIG. 26 shows improved audibility in the predicted aided condition versus unaided condition shown in FIG. 25, i.e. increased Above-threshold contour areas.

Another prediction measurement unique to the present invention, is the measurement of occlusion effect caused by the insertion of the ICP into the ear canal that is characterized by the perceived amplification of the person's own voice. The present invention provides a method of measuring, subjectively and objectively, the magnitude of the occlusion effect. The subjective method is performed by asking the individual wearing the ICP to evaluate his own voice when speaking. If the response is objectionable to the hearing-impaired candidate then an alternative ICP, representing a different hearing aid, may be considered.

The objective method involves the measured response via the probe system in the occluded ear canal and subtracting the occlusion effect reference measurement, i.e. unoccluded ear-canal measurement, as described above.

The patient microphone 57, external to the ear canal, is typically employed to record the individual's own voice during occlusion effect measurements to ensure constant intensity level during both unoccluded and occluded ear canal measurements (see Mueller, H. G., Hawkins, D. B., Northern, J. L., *Probe Microphone Measurements: Hearing Aid Selection and Assessment*, 1992, pp. 221–224). A unique feature of the present invention is to eliminate not the only requirement of constant voice intensity, but also constant voice spectral characteristics. This is accomplished by adjusting the calculated occlusion effect measurement by the difference in the spectral characteristics of the individual's own voice.

It is known in the field of audiology that deep hearing aid insertion substantially reduces the occlusion effect, particularly at low frequencies in the range of 125 to 1000 Hz. Therefore, a smaller ICP, representing a smaller simulated hearing aid, may be used for subsequent evaluation phases.

Figure 27:
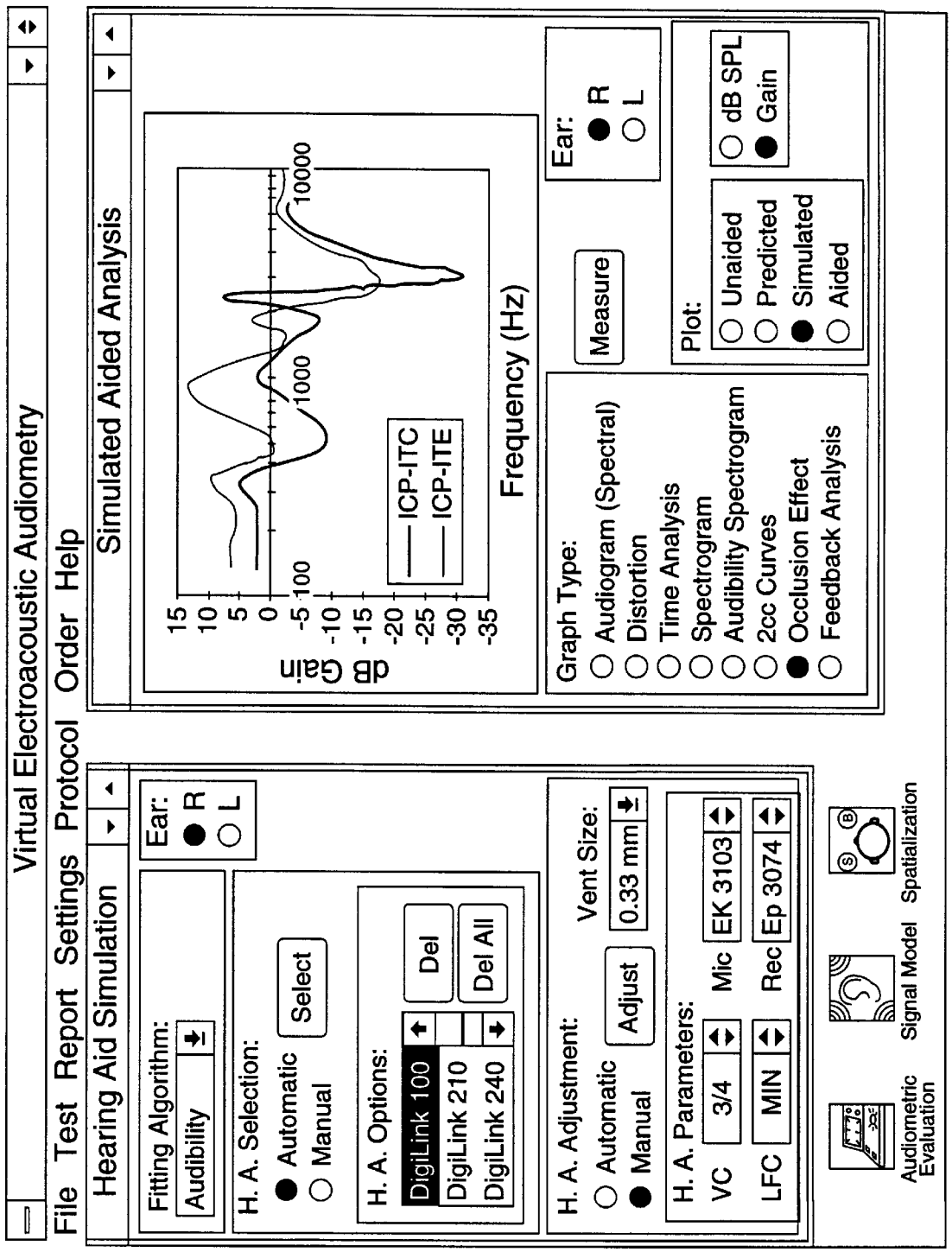
FIG. 27 is a graphic computer generated display showing a simulated aided evaluation module according to the invention.

The occlusion effect created by two types of ICP, i.e. ICP-ITC and ICP-ITE, is shown in the plot of FIG. 27. This plot indicates a significant occlusion effect due to the ICP-ITE versus the ICP-ICP for an individual. This is expected since the ICP-ITE creates a greater residual volume, to which the occlusion effect is known to be directly proportional.

The advantage of ICP measurement at the probe reference point is that all measurements taken are independent of the ICP selected or its placement in the ear canal. However, to present accurate spatialized sounds to the individual, the $H_{icp-rec}(jw)$ transfer measurement is required whenever a new ICP is selected and inserted into the ear canal of the individual.

Figure 37:
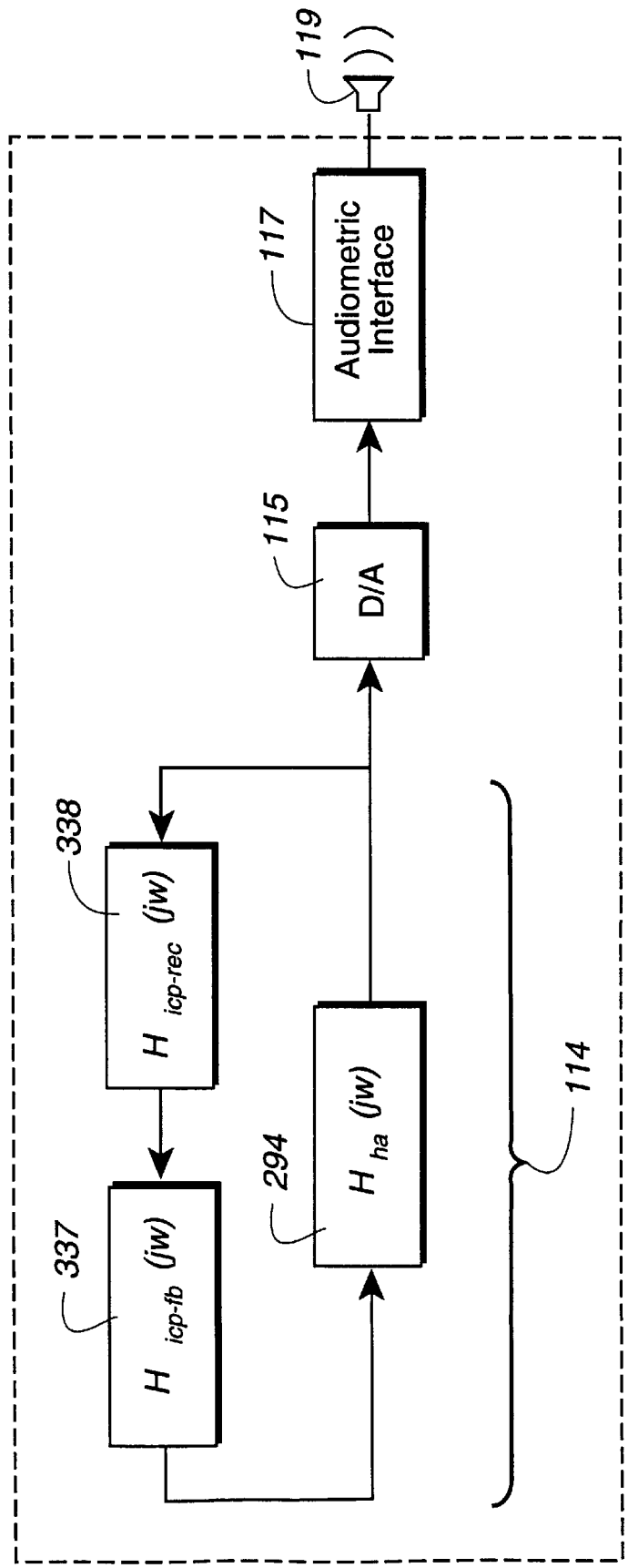
FIG. 37 is a block level schematic diagram showing an example if the prediction and simulation of oscillatory feedback of a simulated hearing aid.

Another measurement unique to the invention is that of acoustic feedback caused by acoustic leakage from the ICP receiver, when simulating a hearing aid receiver, to the face-plate of the ICP, which simulates the face-plate of the hearing aid. The transfer function $H_{icp-fb}(jw)$ (337; FIG. 37), e.g. amplitude and phase response, is measured at the face-plate as described above. The opening created by the removal of the probe tube from the ICP probe tube canal is preferably plugged during the feedback measurement to exclude acoustic leakage due to the probe canal.

A significant application of the feedback transfer function is in the simulation, and thus prediction, of oscillatory feedback of the simulated hearing aid. This undesirable oscillatory feedback manifests itself in the form of whistling, which interferes with the normal operation of the hearing aid. The prediction and simulation of the oscillatory feedback of a simulated hearing aid having a selected setting is accomplished by incorporating the ICP feedback transfer function $H_{icp-fb}(jw)$ 337, as shown in FIG. 37.

Oscillatory feedback can be audible to the individual wearing the ICP via the ICP receiver. The oscillatory feedback can also be measured via the ICP microphone system in conjunction with the VEA system. This feature allows the operating clinician to adjust the settings of the simulated hearing aid, particularly the gain, frequency response, and vent size, such that oscillatory feedback is minimized or eliminated. Similarly, the VEA system can be employed to select automatically an alternate hearing aid or alternate hearing aid parameter set, such that oscillatory feedback is minimized or eliminated.

The predicted aided analysis window also includes other analysis and corresponding plots of Audiogram, Distortion, Time Analysis, Spectrogram, 2-cc Curve. These are standardized measurements and plots that are known to persons skilled in the art of hearing sciences and technology. The 2-cc coupler curves involve conversion of measured in-the-ear-canal response to standard 2-cc coupler curves using real-ear-to-2-cc coupler conversion formulas. Standard signal models, such as pure tones, are typically involved in the 2-cc coupler measurements (see *Specification of Hearing Aid Characteristics*, ANSI-S3.22-1987, American Standards National Institute). Other evaluation methods conceived and well within the means of the invention include the Articulation Index (AI) measures for unaided, predicted aided, simulated aided, and aided conditions.

An objective of the predicted aided module is to predict objectively the performance of a selected hearing aid according to the selected signal model, selected hearing aid parameter set, and the individual's hearing profile, without the involvement of the hearing-impaired individual.

The fourth phase, simulated aided evaluation, is implemented by the simulated aided evaluation module, as shown in FIG. 27. This module allows the operator to select and optimize one or more hearing aids and simulate their audible characteristics. The module consists of a Hearing Aid Simulation window, shown open; a Simulated Aided Analysis window, shown open; a Signal Model window, shown iconized; a Spatialization window, shown iconized; and the Audiometric Evaluation module, shown iconized. The Signal Model, Spatialization, and Audiometric Evaluation windows are essentially identical to those described above. The Simulation Aided window is essentially identical to the Hearing Aid Select/Adjust window of the Predicted Aided Evaluation module. Similarly, the Simulated Aided analysis window is essentially identical to the Predicted Analysis window.

A major difference in the simulated aided evaluation module is the module's ability to synthesize simulated aided conditions and to present the audible results to the hearing-impaired individual. Another significant difference is that analysis is performed by the module based on measured, rather than predicted, data. The measured response is obtained via the microphone probe measurement system with the probe tip placed at the probe reference point, as discussed above.

Figure 34:
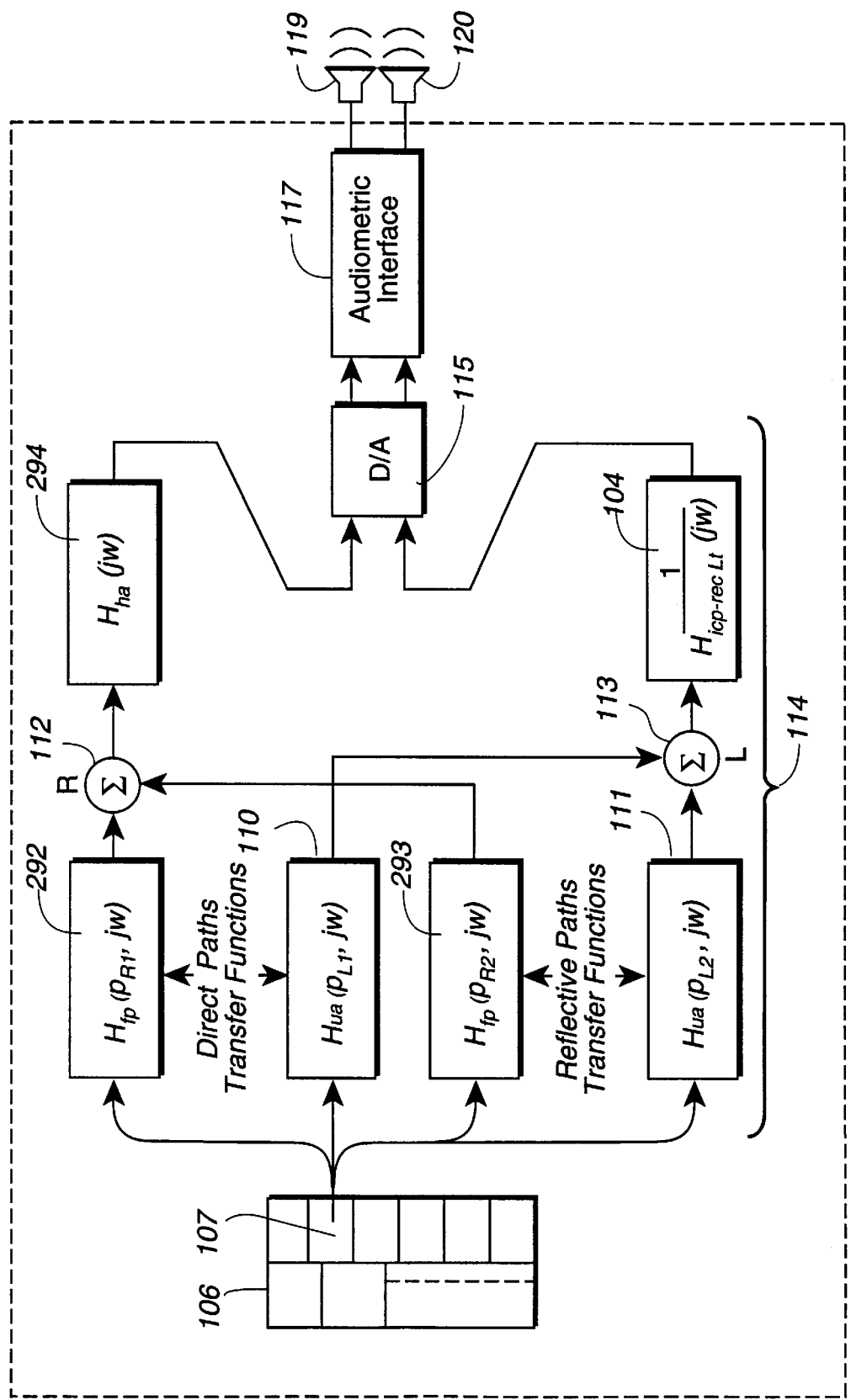
FIG. 34 is a block level schematic diagram showing an example of a teacher-talker/child-listener scenario using simulated aided evaluation for the right ear according to the invention.

An example of a simulated aided signal process, shown in FIG. 34, involves the transfer function of the hearing $H_{ha}$ (jw) that includes the $H_{Rec\text{-}corr}(jw)$, and the face-plate transfer function $H_{fp}(p_n,jw)$ for simulation of the aided ear. The results of the process are converted to analog signals via the digital-to-analog-converter 115 and routed to the right and left ICPs, 119 and 120 respectively, inserted in the ear canals of the individual.

Figure 35:
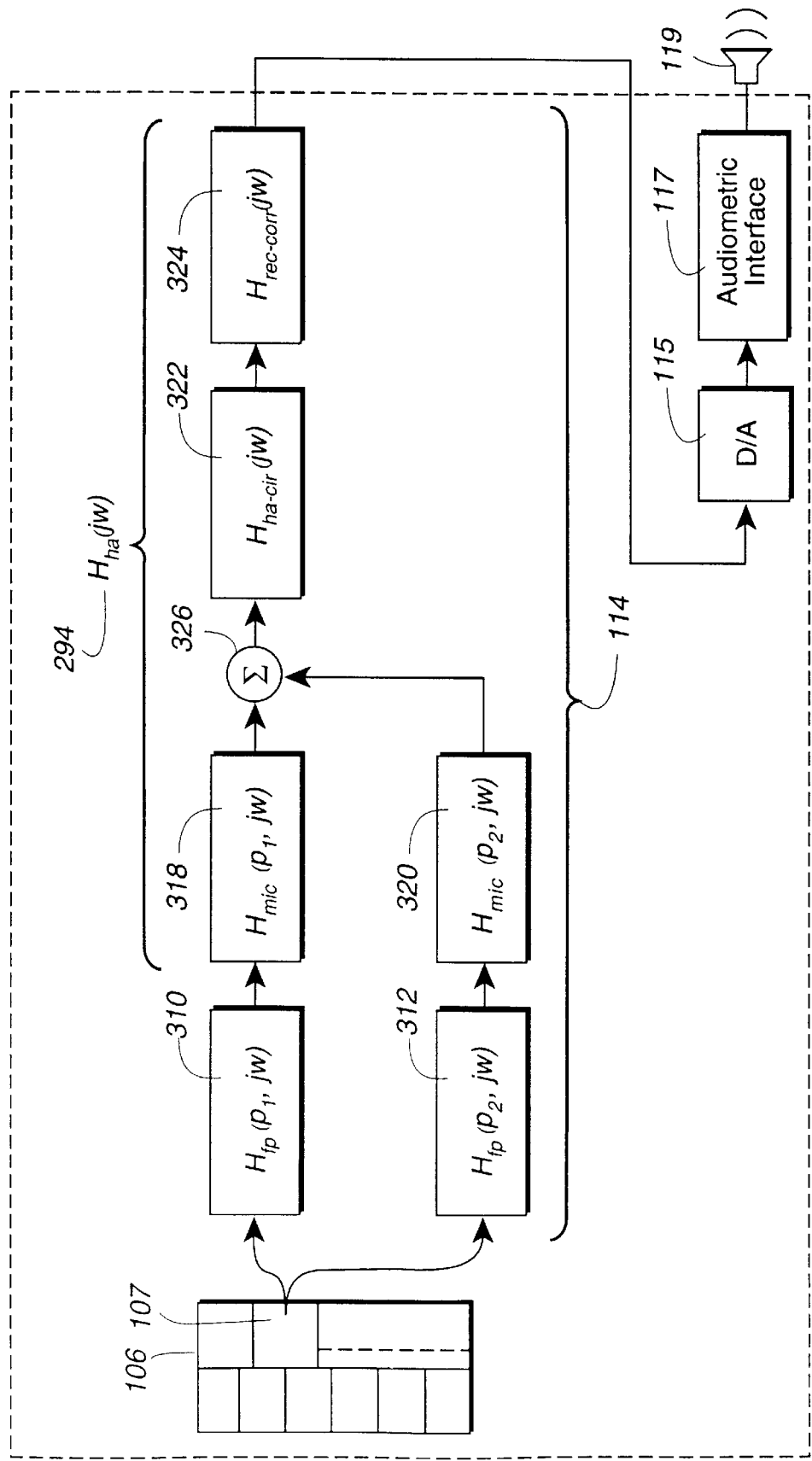
FIG. 35 is a block level schematic diagram showing a simulated hearing aid with directional microphone according to the invention.

If the microphone of the predicted hearing aid is of directional type, then separate microphone transfer functions, representing its directional properties are employed, as shown in FIG. 35. A digital audio file 107 is retrieved from the system memory 106 and processed with face-plate transfer functions $H_{fp}(p_1,jw)$ (310; FIG. 35) and $H_{fp}(p_2,jw)$ (312; FIG. 35), where $p_1$ and $p_2$ represent two points in a three-dimensional space. Signal paths from $p_1$ and $p_2$ may represent direct and primary reflective paths, respectively. Secondary reflective paths $p_3, p_4 \ldots, p_n$ (not shown) can be similarly represented in the digital signal process.

The results of each face-plate transfer function step are further processed with the corresponding microphone transfer function 318, 320 for each signal path from points $p_1, p_2$, ... $p_n$. The results are summed 326 and are processed by the hearing aid circuit transfer function $H_{ha\text{-}cir}(jw)$ 322, $H_{Rec\text{-}corr}(jw)$ 324, as shown in FIG. 35. The resulting digitally processed signal is then converted to analog signal via the digital-to-analog converter 115 and routed to the appropriate ICP within the ear canal via the audiometric transducer interface 117.

The simulated aided analysis window includes measurements and corresponding plots of Audiogram, Distortion, Time Analysis, Spectrogram, Audibility Spectrogram, 2-cc Curve, Occlusion Effects, and Feedback Analysis. These measurements are essentially identical to those described above for the predicted analysis window. This process is based on the system's ability to compute a hearing aid prescription based on a selected fitting prescription formula/rational. The selected hearing aid can be adjusted and results analyzed and plotted with or without the involvement of the hearing-impaired individual.

An objective of the simulated aided module is to optimize, objectively and subjectively, the performance of a selected hearing aid according to measured in-the-ear-canal probe response as a function of the selected signal model, hearing aid parameter set, the individual's measured hearing profile, and subjective responses to the presented audible signal.

One feature unique to the invention is the ability to compute the characteristics of a simulated monaural or binaural hearing aid system that produces natural sound perception and improved sound localization ability to the hearing impaired individual. This is accomplished by selecting a simulated hearing aid transfer function that produces, in conjunction with the face-plate transfer function, a combined transfer function that matches that of the unaided transfer function for each ear. The matching requirement typically involves frequency and phase responses. However, the magnitude response is expected to vary because most hearing impaired individuals require amplification to compensate for their hearing losses.

Once the hearing aid selection and optimization processes are completed via VEA system simulation, the characteristics of the simulated hearing aid are translated to hearing aid specifications for manufacture/assembly. Manufacturing specifications include: hearing aid components simulated by the VEA system, including the microphone and receiver; shape and size of hearing aid according to the ICP selected; hearing aid circuit blocks and circuit components; hearing aid parameter setting; and vent type/size. An objective of the VEA system is to provide a detailed specification to the manufacturer/assembler to manufacture/assemble a monaural or binaurally matched hearing aid system that closely matches the preferred simulated hearing aid. Ordering of the actual hearing aid is performed from the Order menu shown in FIG. 27 which provides a printout of detailed hearing aid specification.

Figure 28:
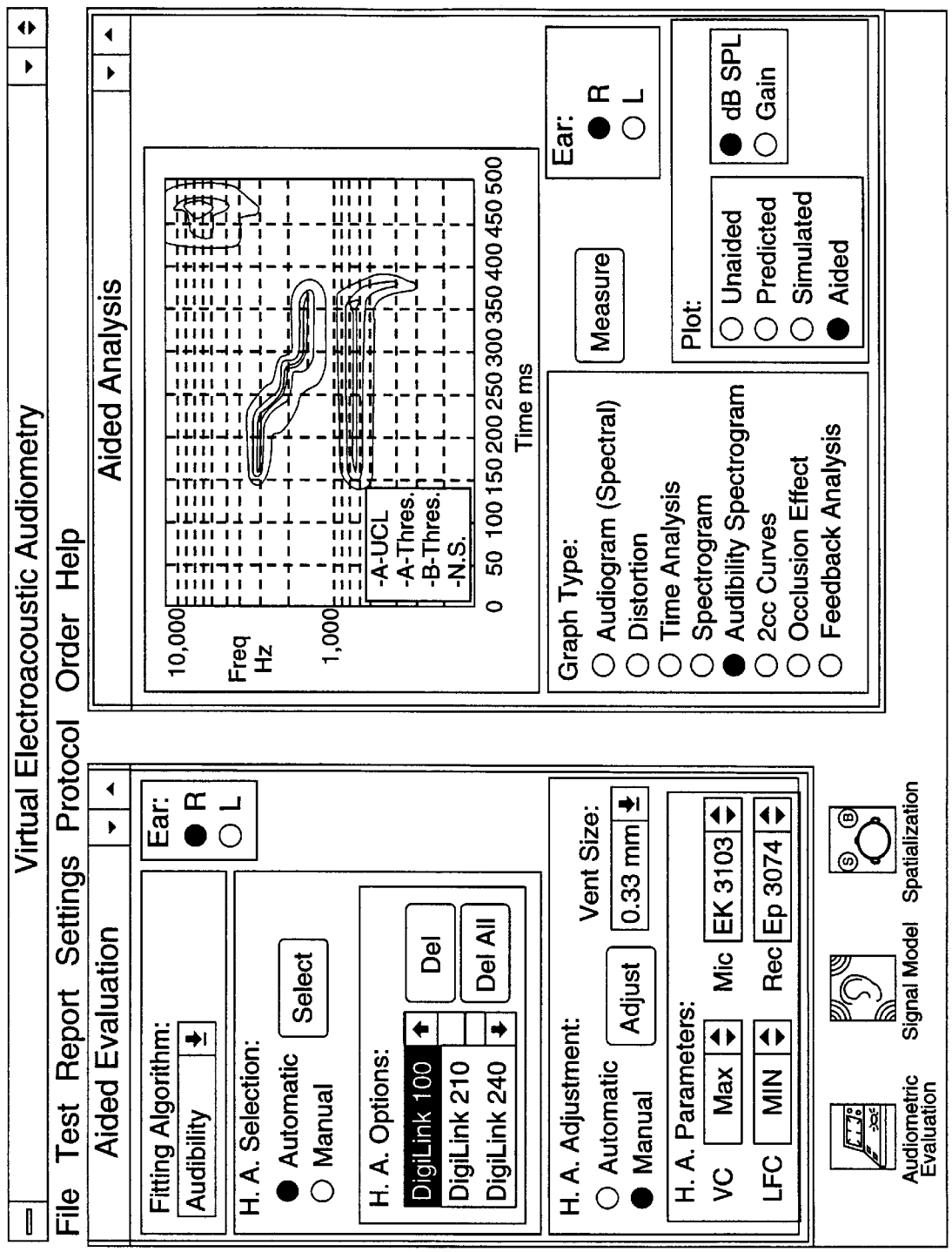
FIG. 28 is a graphic computer generated display showing an aided evaluation module according to the invention.

The final step in the process, aided evaluation, is represented by the aided evaluation module as shown in FIG. 28. This module consists of an Aided Evaluation window, shown open, an Aided Analysis window, shown open; an Audiometric Evaluation window, shown iconized; a Signal Model window, shown iconized; and a Spatialization window, shown iconized. The latter three windows are essentially identical to those in the predicted aided evaluation and simulated aided evaluation windows. The aided evaluation window permits electronic adjustment of manufactured hearing aid parameters as in the case of a programmable hearing aid, shown in FIG. 21, or displaying the suggested parameter setting in the case of a manually adjusted hearing aids, shown in FIG. 20.

The aided analysis window is similar to the analysis window for unaided, predicted aided, and simulated aided evaluation process steps, except that the measurements and corresponding plots reflect the response from the actual hearing aid inserted in the ear canal of the individual rather than predicted or synthesized signal, i.e. simulated aided, response analysis.

Figure 36:
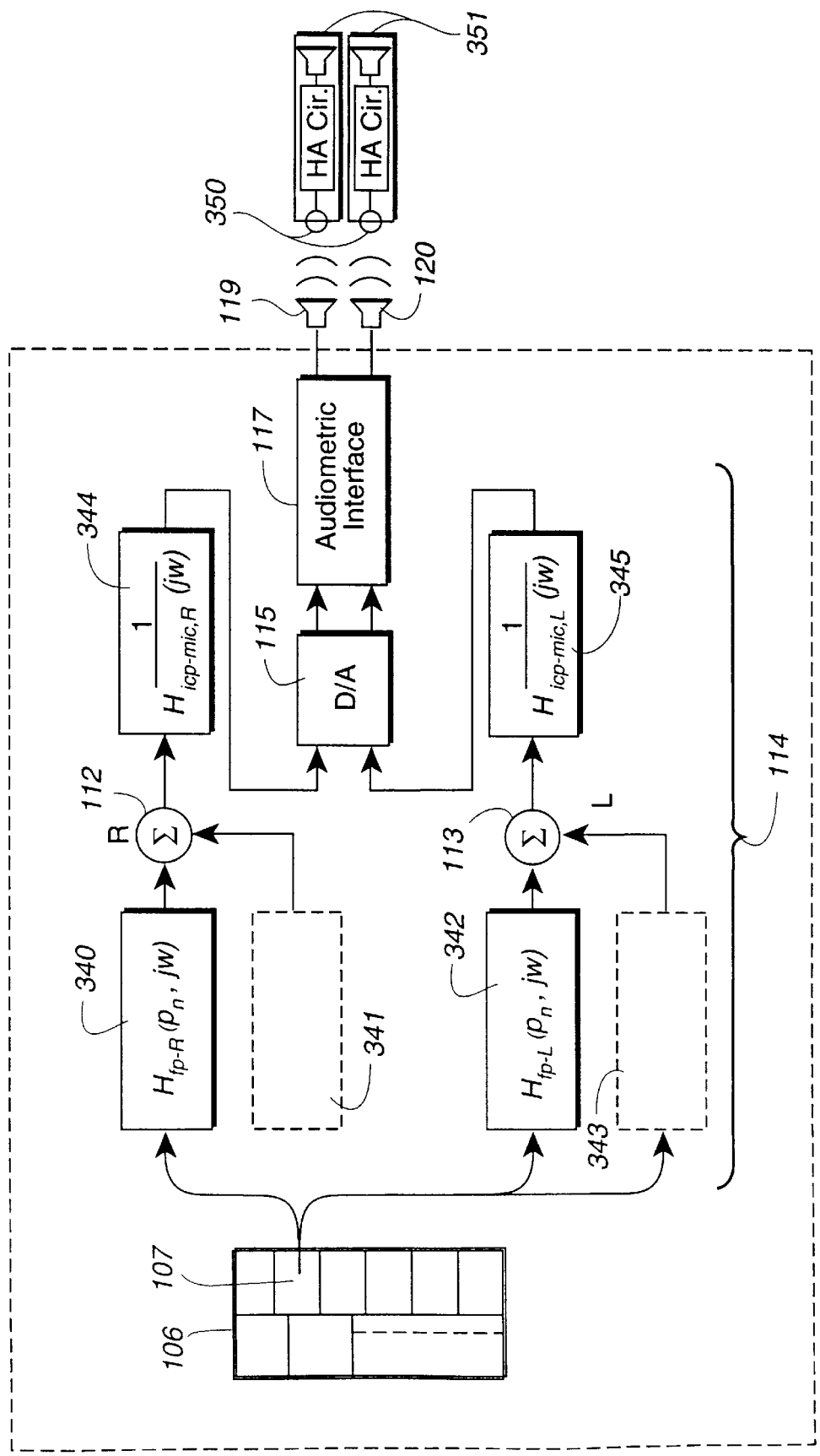
FIG. 36 is a block level schematic diagram showing an example of the realization of realistic listening scenarios for aided hearing evaluation conditions according to the invention.

Synthesized realistic acoustic signals are presented to the hearing aid by coupling spatialized sounds directly to the microphone of the hearing aid, as shown in FIGS. 19–21. The face-plate transfer function, $H_{fp}(p_n,jw)$, and the supplied ICP receiver-to-microphone transfer function $H_{icp\text{-}mic}(jw)$ are employed in the digital synthesis process, as shown in FIG. 36. A digital audio file 107 representing an audio source at location $p_n$ in space is retrieved from the system memory 106 for processing with the free-field to face-plate transfer function $H_{fp}(p_n,jw)$ 340, 342 for right and left ears, individually. Other parallel processes reflecting filtering of additional audio sources or filtering of reflective paths, shown collectively in the dashed rectangles 341, 343, are summed with the right 112 and left 113 summing nodes. The outcome of summing nodes is further processed to equalize the ICP receiver to hearing aid microphone coupling effects by applying the inverse transfer function $1/H_{icp\text{-}mic}(jw)$ 344, 345. The acoustic signals supplied to the microphones 350 of the hearing aids 351 represent spatialized signals with characteristics selected and controlled by the VEA system operator via the Spatialization, Signal Module, and Audiometric Evaluation windows.

Electroacoustic testing of the hearing aid, coupled with the ICP as described above, may also be performed external to the ear canal, for example 2-cc coupler measurements can be performed by connecting the receiver output of the hearing aid to the 2-cc coupler input. The ICP, in conjunction with the signal generation capability of the VEA, can produce various acoustic stimuli as input to the hearing aid during its 2-cc coupler-based hearing aid evaluation. Similarly, 2-cc coupler measurements can be performed on the ICP, i.e. a simulated hearing aid, by connecting the receiver output of the ICP to the 2-cc coupler input.

The invention not only deals effectively with today's diagnostic and fitting problems but also provides a basis for new tools that are audiologically significant. For example, the system's ability to synthesize realistic acoustic conditions, both simulated aided and aided, can be used as an auditory rehabilitative tool where a hearing impaired listening ability is improved by interactive training. In such application, the hearing impaired person is presented with spatialized signals that represent spoken words in noisy background. Even though the words might be audible as determined from the audibility measurements and methods described above, these words might not be intelligible for the untrained hearing-impaired individual. Depending on the verbal response, or registered response via a response keypad, the VEA system can provide audible or visual feedback to the hearing impaired individual that indicates the appropriateness of the response. The object of this new test is to teach the hearing-impaired how to improve speech perception and intelligibility beyond mere audibility.

Another test made possible by the invention determines the individual's ability to localize a sound in a plane or in three-dimensional space. An example is the detection of minimal audible angle (MAA) test whereby the individual's ability to detect, in degrees, the minimal angular separation of pure tones versus frequency (see Mills, A. W., *On the Minimum Audible Angle*, Journal of Acous. Soc. of Am. 30:237–246, 1956). Furthermore, a comparison of the individual's localization ability can be compared across unaided, simulated aided, and aided conditions.

The invention also makes it possible to determine the individual's ability to detect sound movements in a plane or in a three-dimensional space. For example, a sound object can be synthesized to represent movement in a particular geometrical and frequency pattern. The individual's impaired ability to detect the movement can be assessed. Furthermore, a comparison of the individual's ability to detect sound movements can be compared across various listening conditions in the unaided, simulated aided, and aided conditions.

Although the invention is described herein with reference to the preferred embodiment, one skilled in the art will readily appreciate that other applications may be substituted for those set forth herein without departing from the spirit and scope of the present invention. Accordingly, the invention should only be limited by the Claims included below.

I claim:

1. A system for assessment of the hearing function in humans, comprising:
   a virtual electroacoustic audiometer comprising:
      an audiometric module comprising means for selective syntheses of acoustic signals for hearing diagnostics, hearing aid prescription, hearing aid simulation, and hearing aid fitting; and
   an intracanal prostheses that emulates a hearing aid prostheses, said intracanal prostheses containing:
      a receiver coupled to said audiometric module for delivering said acoustic signals in-the-ear-canal near the tympanic membrane; and
      means for measuring in-the-ear-canal acoustic response to said acoustic signals near the tympanic membrane during hearing evaluation.

2. The system of claim 1, further comprising:
   means for performing said assessment in terms representing absolute sound pressure level.

3. The system of claim 1, further comprising:
   means for performing hearing aid simulation by incorporating electroacoustic transfer functions into the digital synthesis of an acoustic signal.

4. The system of claim 3, further comprising:
   means for applying a hearing aid transfer function during syntheses of audio signals, including primary audio signals comprising pure tones and speech, and secondary audio signals comprising background noise and other competing sources.

5. The system of claim 3, further comprising:
   means for synthesizing audio signals, including primary audio signals comprising pure tones and speech, and secondary audio signals comprising background noise and other competing sources for hearing evaluation with any of a hearing aid and a simulated hearing aid.

6. The system of claim 1, further comprising:
   means for simulating any of a hearing aid occlusion effect, venting effects, and oscillatory feedback potential.

7. The system of claim 1, further comprising:
   means for applying at least one transfer function to synthesize spatialized acoustic signals and create realistic listening environments in a multi-dimensional acoustic space.

8. The system of claim 1, further comprising:
   a digital audio synthesis module for generating an acoustic signal.

9. The system of claim 1, further comprising:
   a digital audiometer module for communicating acoustic information between said intracanal prostheses and said virtual electroacoustic audiometer.

10. The system of claim 1, further comprising:
    a virtual acoustic space measurement module for generating at least one acoustic transfer function to allow synthesis of spatialized acoustic signals.

11. A system for assessment of the hearing function in humans, comprising:
    an intracanal prostheses that emulates a hearing aid prostheses, said intracanal prostheses containing:
       a receiver coupled to an audiometric module for delivering acoustic signals generated by said audiometric module in-the-ear-canal near the tympanic membrane; and
       means for measuring in-the-ear-canal acoustic response to said acoustic signals near the tympanic membrane during hearing evaluation; and
    a virtual electroacoustic audiometer comprising said audiometric module, said audiometric module comprising means for synthesis of acoustic signals representative of realistic listening environments in a multi-dimensional space for hearing diagnostics, hearing aid prescription, hearing aid simulation, and hearing aid fitting, said virtual electroacoustic audiometer comprising:
       a digital audio synthesis module for generating said acoustic signals;
       means for performing hearing aid simulation, said means for performing hearing aid simulation comprising means for incorporating electroacoustic transfer functions into the digital synthesis of an acoustic signal for hearing diagnostics, hearing aid prescription, hearing aid simulation, and hearing aid fitting; and
       a virtual acoustic space measurement module for generating at least one acoustic transfer function for synthesizing spatialized acoustic signals.

12. The system of claim 11, further comprising:
    means for performing hearing aid simulation by incorporating electroacoustic transfer functions into the digital synthesis of an acoustic signal.

13. The system of claim 11, further comprising:
    means for applying a hearing aid transfer function to synthesize audio signals, including primary audio signals comprising pure tones and speech, and secondary audio signals comprising background noise and other competing sources.

14. The system of claim 11, further comprising:

means for simulating any of a hearing aid occlusion effect, venting effects, and oscillatory feedback potential.

15. A system for assessment of the hearing function in humans, comprising:

a virtual electroacoustic audiometer comprising:

an audiometric module comprising means for selective synthesis of acoustic signals that are representative of realistic listening environments in a multi-dimensional space for hearing diagnostics, hearing aid prescription, hearing aid simulation, and hearing aid fitting, said virtual electroacoustic audiometer comprising:

a digital audio synthesis module comprising means for generating said acoustic signals;

means for performing hearing aid simulation, said means for performing hearing aid simulation comprising means for incorporating electroacoustic transfer functions into the digital synthesis of an acoustic signal for hearing diagnostics, hearing aid prescription, hearing aid simulation, and hearing aid fitting; and a virtual acoustic space measurement module for generating at least one acoustic transfer function for synthesizing spatialized acoustic signals.

16. The system of claim 15, wherein said virtual acoustic space measurement module measures individualized transfer functions that include any of an individual's acoustic effects of body, head, external ear, and face plate on incoming acoustic signals from a multi-dimensional acoustic space.

17. A system for assessment of the hearing function in humans, comprising:

a virtual electroacoustic audiometer comprising:

an audiometric module comprising means for selective syntheses of acoustic signals representative of realistic listening environments in a multi-dimensional space for hearing diagnostics, hearing aid prescription, hearing aid simulation, and hearing aid fitting; and an intracanal prostheses that emulates a hearing aid prostheses, said intracanal prostheses containing:

a receiver coupled to said audiometric module for delivering said acoustic signals in-the-ear-canal near the tympanic membrane; and:

means for measuring in-the-ear-canal acoustic response to said acoustic signals near the tympanic membrane during hearing evaluation;

wherein said system provides simultaneous signal delivery and measurement within the ear canal near the tympanic membrane.

18. The system of claim 17, wherein said measurements are performed at a common reference point near the tympanic membrane during all phases of hearing aid fitting to directly correlate measurement data.

19. A method for in situ simulation of at least one hearing aid prostheses, comprising the steps of:

selectively simulating electroacoustic parameters of hearing aid prostheses with a virtual electroacoustic audiometer comprising an audiometric module, said electroacoustic parameters including:

a. signal processing parameters, including gain, frequency response, filtering, and signal adaptation to incoming sound; and b. acoustic parameters, including venting effects, insertion depth effects, oscillatory feedback potential, and occlusion effects; and simulating physical parameters of a hearing aid including hearing aid fit and comfort with an intracanal prostheses that is coupled to said audiometric module, and positioning said intracanal prostheses in-the-ear-canal near the tympanic membrane; and emulating a hearing aid prostheses with said intracanal prostheses.

20. A method for assessment of the hearing function in humans, comprising the steps of:

synthesizing acoustic signals with a virtual electroacoustic audiometer comprising an audiometric module for hearing diagnostics, hearing aid prescription, hearing aid simulation, and hearing aid fitting; and delivering said acoustic signals and measuring in-the-ear-canal acoustic response near the tympanic membrane with an intracanal prostheses that emulates a hearing aid prostheses, said intracanal prostheses containing a receiver coupled to an audiometric module for delivering said acoustic signals in-the-ear-canal near the tympanic membrane.

21. The method of claim 20, further comprising the step of:

measuring in situ the occlusion effect due to the insertion of a simulated hearing aid.

22. The method of claim 20, further comprising the step of:

fitting a hearing aid based on subjective response and in situ measured response to signal models that are spatialized according to spatialization parameters and according to an individual's transfer functions.

23. The method of claim 20, further comprising the step of:

directly coupling acoustically said intracanal prostheses to a hearing aid microphone for hearing aid evaluation and in situ aided hearing evaluation.

24. The method of claim 20, further comprising the step of:

predicting and simulating the occurrence of oscillatory feedback.

25. The method of claim 24, wherein said predicting and simulating step incorporates a measured acoustic feedback transfer function.

26. The method of claim 20, further comprising the step of:

providing hearing aid specifications based on simulated hearing aid characteristics that are interactively developed and optimized by synthesizing said acoustic signals, and by simultaneously measuring the acoustic response near the tympanic membrane.

27. The method of claim 20, further comprising the step of:

selecting and specifying a hearing aid system which produces natural sound perception by matching in situ acoustic response characteristics of said hearing aid system to that of an unaided response in a multi-dimensional acoustic space.

28. The method of claim 27, further comprising the step of:

testing said hearing aid in a synthesized realistic acoustic environment.

29. The method of claim 20, further comprising the step of:

evaluating and optimizing an individual's ability to detect movement of sounds in a multi-dimensional space.

30. The method of claim 20, further comprising the step of:

evaluating and optimizing an individual's ability to localize sounds in a multi-dimensional space.

31. The method of claim 20, further comprising the steps of:

measuring acoustic response of an individual's own voice in an occluded ear canal via said intracanal prosthesis; and subtracting an unoccluded ear canal reference measurement therefrom; wherein an objective measure for occlusion effect is calculated.

32. A method for estimating the occlusion effect of a simulated hearing aid, comprising the steps of:

measuring acoustic response in the ear canal near the tympanic membrane of an individual, where said ear canal is occluded by an intracanal prosthesis that is coupled to an audiometric module and that emulates said simulated hearing aid; and subtracting an unoccluded ear canal reference measurement therefrom, wherein an objective measure for occlusion effect is calculated.

* * * * *